United States Patent
Sasayama et al.

(10) Patent No.: US 10,793,822 B2
(45) Date of Patent: Oct. 6, 2020

(54) CONCENTRATING DEVICE AND METHOD FOR CONCENTRATING CELL SUSPENSION

(71) Applicants: Nipro Corporation, Osaka-shi, Osaka (JP); Norihisa Sasayama, Osaka (JP); Masakatsu Takeuchi, Osaka (JP); Atsushi Taguchi, Osaka (JP)

(72) Inventors: Norihisa Sasayama, Osaka (JP); Masakatsu Takeuchi, Osaka (JP); Atsushi Taguchi, Osaka (JP)

(73) Assignee: NIPRO CORPORATION (JP)

( * ) Notice: Subject to any disclaimer, the term of this patent is extended or adjusted under 35 U.S.C. 154(b) by 353 days.

(21) Appl. No.: 15/574,530

(22) PCT Filed: May 24, 2016

(86) PCT No.: PCT/JP2016/065331
§ 371 (c)(1),
(2) Date: Nov. 16, 2017

(87) PCT Pub. No.: WO2016/190313
PCT Pub. Date: Dec. 1, 2016

(65) Prior Publication Data
US 2018/0148680 A1    May 31, 2018

(30) Foreign Application Priority Data
May 25, 2015 (JP) ................. 2015-105863

(51) Int. Cl.
*C12M 1/00* (2006.01)
*C12M 1/10* (2006.01)
(Continued)

(52) U.S. Cl.
CPC ............. *C12M 47/02* (2013.01); *B01D 63/02* (2013.01); *B01D 63/04* (2013.01); *B01D 63/16* (2013.01);
(Continued)

(58) Field of Classification Search
CPC ...... C12M 47/02; C12M 29/16; C12M 29/04; C12M 41/48; C12M 23/50; C12M 23/14;
(Continued)

(56) References Cited

U.S. PATENT DOCUMENTS

2013/0244322 A1   9/2013  Henon
2016/0168529 A1   6/2016  Taniguchi et al.

FOREIGN PATENT DOCUMENTS

JP   2005169181 A   6/2005
JP   2005323534 A   11/2005
(Continued)

OTHER PUBLICATIONS

English translation of JP 2005-169181, accessed Dec. 2019 (Year: 2019).*

*Primary Examiner* — William H. Beisner
*Assistant Examiner* — Danielle B Henkel
(74) *Attorney, Agent, or Firm* — Jordan and Koda, PLLC

(57) ABSTRACT

A means capable of simply and efficiently concentrating a cell suspension. A concentrator has a culture vessel having a first port and a second port, a server bag having a port, a case having a hollow fiber bundle in the internal space, a filtering device having an inlet port, a first outlet port, and a second outlet port, a collection vessel having a port, a liquid supply circuit connected to the first port, the inlet port, and the server bag's port so that flow passages are switchable, a liquid discharge circuit connected to the second port, the first outlet port, the second outlet port, and the collection vessel's port so that flow passages are switchable, a liquid supply mechanism having a switching mechanism, a supply pump, and a discharge pump, and a rotation mechanism rotating the filtering device.

12 Claims, 26 Drawing Sheets

(51) Int. Cl.
| | |
|---|---|
| *C12M 3/06* | (2006.01) |
| *C12M 3/00* | (2006.01) |
| *B01D 63/02* | (2006.01) |
| *C12M 3/04* | (2006.01) |
| *C12M 3/02* | (2006.01) |
| *B01D 63/04* | (2006.01) |
| *B01D 63/16* | (2006.01) |
| *C12M 1/36* | (2006.01) |
| *B01D 61/24* | (2006.01) |

(52) U.S. Cl.
CPC ............... *C12M 1/10* (2013.01); *C12M 3/02* (2013.01); *C12M 3/043* (2013.01); *C12M 3/06* (2013.01); *C12M 3/065* (2013.01); *C12M 23/14* (2013.01); *C12M 23/42* (2013.01); *C12M 23/44* (2013.01); *C12M 23/50* (2013.01); *C12M 29/04* (2013.01); *C12M 41/48* (2013.01); *B01D 61/243* (2013.01); *B01D 2313/06* (2013.01); *B01D 2313/10* (2013.01); *B01D 2313/12* (2013.01); *B01D 2315/02* (2013.01); *B01D 2315/18* (2013.01); *C12M 29/16* (2013.01)

(58) Field of Classification Search
CPC ...... C12M 3/043; C12M 3/065; C12M 23/42; C12M 23/44; C12M 1/10; C12M 3/06; C12M 3/02; B01D 2313/06; B01D 2315/18; B01D 61/243; B01D 2315/02; B01D 2313/12; B01D 2313/10; B01D 63/16; B01D 63/04; B01D 63/02
See application file for complete search history.

(56) References Cited

FOREIGN PATENT DOCUMENTS

| JP | 2012210187 A | 11/2012 |
|---|---|---|
| WO | 2014119529 A1 | 8/2014 |
| WO | 2015012174 A1 | 1/2015 |
| WO | 2016060209 A1 | 4/2016 |
| WO | 2017112455 A2 | 6/2017 |

\* cited by examiner

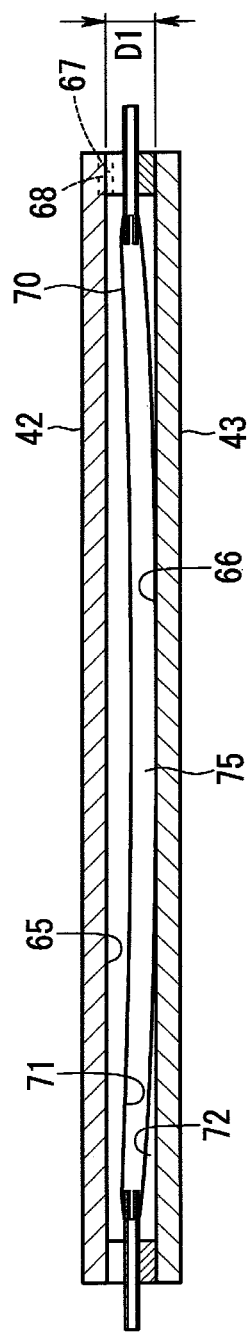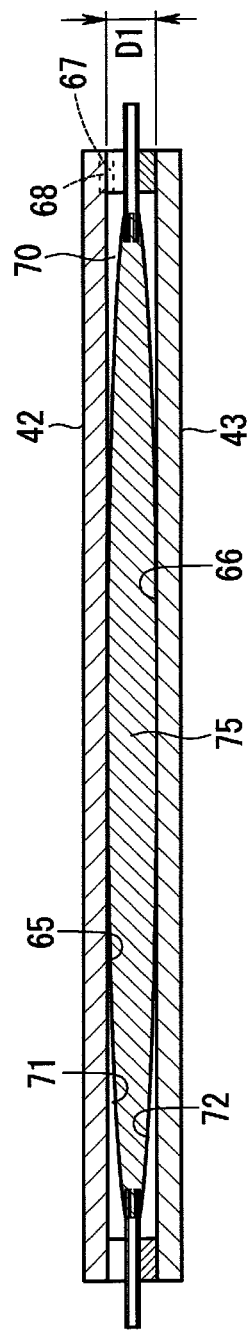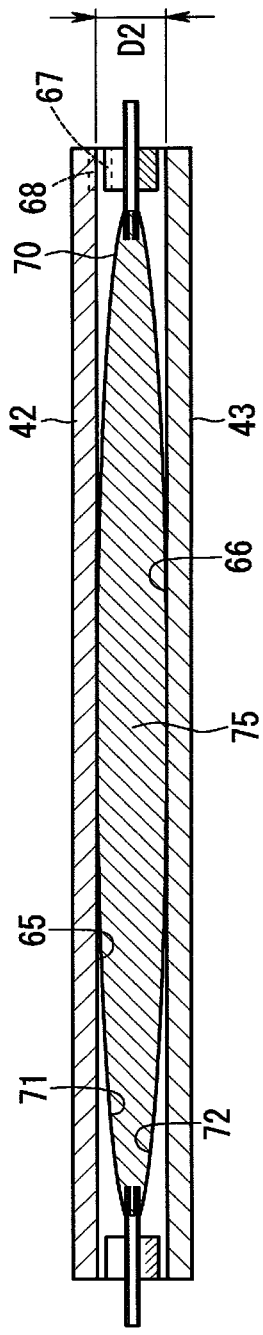

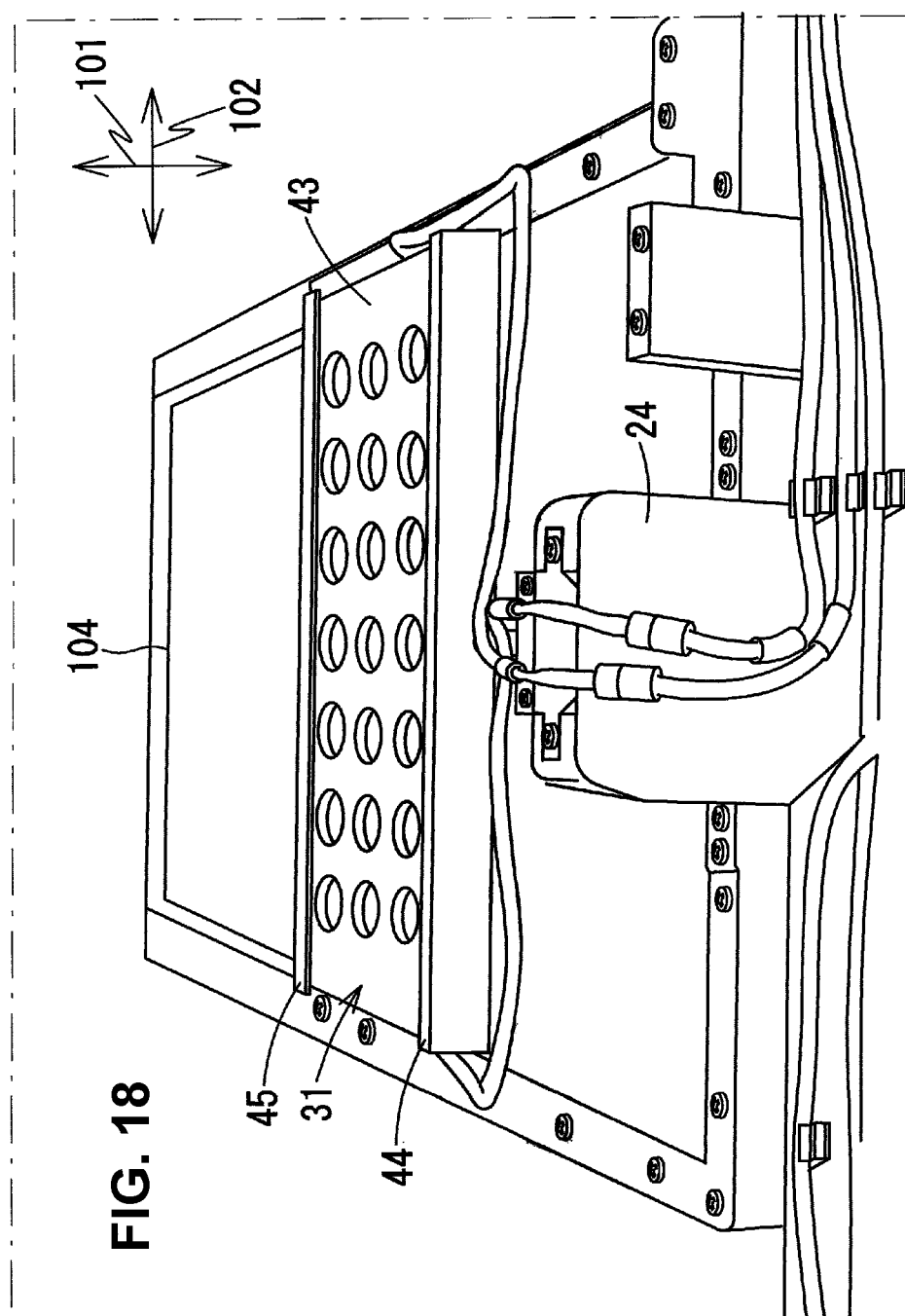

CONCENTRATING DEVICE AND METHOD FOR CONCENTRATING CELL SUSPENSION

BACKGROUND OF THE INVENTION

The present invention relates to a concentrator concentrating a cell suspension and a method for concentrating a cell suspension.

Cell culture includes a process of transferring cells in a culture vessel to another culture vessel and a process of exchanging culture media in a culture vessel. Such processes of the cell culture need to be performed in an aseptic state. The cell culture is performed over several day to several weeks, and, during this period, each process is repeatedly performed. For the purpose of saving labor and culturing a large number of cells in cell culture, a device performing each process in cell culture is known (Patent Document 1).

For storage or transplantation of cells, for example, the concentration (number of cells per capacity) of cells in a cell suspension containing cultured cells is increased in some cases. As a method for concentrating a cell suspension, a method is known which uses a cell suspension treating device which has a hollow fiber separation membrane and is an inner pressure filtration system (Patent Document 2).

CITATION LIST

Patent Literatures

Patent Document 1: Japanese Patent Laid-Open No. 2009-291104
Patent Document 2: Japanese Patent Laid-Open No. 2012-210187

SUMMARY OF INVENTION

A technique using a centrifugal separator as in a cell concentrator described in Patent Document 1 requires a space where a centrifugal separator is placed. Moreover, a space held in an aseptic state for moving a cell suspension from a culture vessel to a vessel suitable for centrifugal separation is required. Furthermore, a robot arm for treating a centrifugal separator requires a complicated motion, which has posed a problem that the device is complicated and the size increases. A cell suspension treating device described in Patent Document 2 is small as compared with the centrifugal separator but is not fully automated, and thus is not suitable for culturing and concentrating a large number of cells.

The present invention has been made in view of the above-described circumstances. It is an object of the present invention to provide a means capable of simply concentrating a cell suspension.

(1) A concentrator according to the present invention has a filtering device having a case provided with a filtration membrane in the internal space, an inflow port and a first outflow port bringing the inside of the filtration membrane and an outside of the case into communication with each other, and a second outflow port bringing the outside of the filtration membrane and an outside into communication with each other, a liquid supply circuit connected to the inflow port, a liquid discharge circuit connected to the first outflow port and the second outflow port, and a first rotation mechanism rotating the filtering device so that the positions in the vertical direction of the inflow port and the first outflow port are changeable.

The filtering device allows a liquid to flow in through the liquid supply circuit. Moreover, the filtering device allows a liquid to flow out through the liquid discharge circuit. Each of the inflow and the outflow of the liquid in/from the filtering device is performed through a different port and the inflow and the outflow of the liquid in/from the filtering device are separated into the liquid supply circuit and the liquid discharge circuit, which reduces a possibility that a liquid which is caused to flow out of another vessel or device is mixed with a liquid which is caused to flow in the filtering device.

For example, the gravity is utilized in priming of the filtering device or the concentration of a cell suspension using the filtering device. In the priming of the filtering device, a priming liquid is caused to flow in from a port located downward in the filtering device and gas is discharged from a port located upward in the filtering device. In the concentration of the cell suspension, the cell suspension is caused to flow in from the port located upward in the filtering device and cells trapped by the filtration membrane descend downward in the filtering device by gravity.

Since the rotation mechanism rotates the filtering device so that the positions in the vertical direction of the inflow port and the first outflow port of the filtering device are changeable, the positions in the vertical direction of the inflow port and the first outflow port can be changed as appropriate in the priming or the concentration of the cell suspension. This eliminates the necessity of discharging gas and a liquid from the inflow port or causing a liquid to flow in from the first outflow port. Moreover, in the concentration of the cell suspension, cells contained in the cell suspension descend in the internal space of the filtration membrane by the action of the gravity, and thus the entire filtration membrane can be efficiently used.

(2) Preferably, the concentrator further has a culture vessel having a first port and a second port bringing an internal space and the outside into communication with each other, a first reservoir having a third port bringing the internal space and the outside into communication with each other, a collection vessel having a fourth port bringing an internal space and the outside into communication with each other, and a liquid supply/discharge mechanism having a switching mechanism switching flow passages in the liquid supply circuit and the liquid discharge circuit, a first pump circulating a liquid in the liquid supply circuit, and a second pump circulating a fluid in the liquid discharge circuit, in which the liquid supply circuit is connected to the first port, the inflow port, and the third port so that the flow passages are switchable and the liquid discharge circuit is connected to the second port, the first outflow port, the second outflow port, and the fourth port so that the flow passages are switchable.

The culture vessel, the first reservoir, and the filtering device allow a liquid to flow in through the liquid supply circuit. Moreover, the culture vessel and the filtering device allow a liquid to flow out through the liquid discharge circuit. Moreover, the collection vessel allows a liquid to flow in from the filtering device through the liquid discharge circuit. Moreover, each of the inflow and the outflow of a liquid in/from the culture vessel and the filtering device is performed through a different port. Thus, the inflow and the outflow of a liquid in/from each vessel or device are separated into the liquid supply circuit and the liquid discharge circuit, which reduces a possibility that a liquid which is caused to flow out of each vessel or device is mixed with a liquid which is caused to flow in each vessel or device.

(3) Preferably, a second rotation mechanism rotating the culture vessel so that the positions in the vertical direction of the first port and the second port are changeable is further provided.

Thus, the culture vessel can be brought into a position suitable for causing a liquid to flow in the culture vessel or discharging a liquid and gas from the culture vessel.

(4) Preferably, the rotation mechanism rotates the culture vessel so that the positions in the vertical direction of the first port and the second port are changeable and integrally rotates the culture vessel and the filtering device.

Thus, the size of the filtering device is reduced.

(5) Preferably, a second reservoir having a fifth port bringing an internal space and the outside into communication with each other and capable of reserving a priming liquid in the internal space, a third reservoir having a sixth port bringing an internal space and the outside into communication with each other and capable of reserving a culture medium in the internal space, and a control portion controlling an operation of the liquid supply/discharge mechanism and the rotation mechanism are further provided, in which the liquid supply circuit is connected to the fifth port and the sixth port so that the flow passages are switchable, and the control portion executes a moving step of bringing the second port and the third port into communication with each other by the liquid supply/discharge mechanism, and then driving the first pump to thereby move the cell suspension to the first reservoir from the culture vessel, a priming step of bringing the filtering device into a first state in which the inflow port is located downward relative to the first outflow port by the rotation mechanism, bringing the fifth port and the inflow port into communication with each other by the liquid supply/discharge mechanism and opening the inflow port, and then driving at least the first pump to thereby supply the priming liquid to the filtering device from the second reservoir, a filtering step of bringing the filtering device into a second state in which the inflow port is located upward relative to the first outflow port by the rotation mechanism, bringing the third port and the inflow port into communication with each other by the liquid supply/discharge mechanism, closing the first outflow port and opening the second outflow port, and then driving at least the first pump to thereby supply the cell suspension to the filtering device from the first reservoir, and a collecting step of bringing the sixth port and the inflow port into communication with each other by the liquid supply/discharge mechanism, closing the second outflow port and bringing the first outflow port and the fourth port into communication with each other, and then driving at least the first pump to thereby supply the cell suspension to the collection vessel from the filtering device.

By the moving step, the cell suspension is caused to flow in the first reservoir from the culture vessel. By the priming step, the priming liquid is supplied to the inflow port of the filtering device from the second reservoir. In the priming step, the inflow port is located downward relative to the first outflow port in the filtering device, and therefore gas present inside the filtering device is discharged from the first outflow port. By the filtering step, the cell suspension is supplied to the inflow port of the filtering device from the first reservoir. In the filtering step, the inflow port is located upward relative to the first outflow port in the filtering device, and therefore the cells contained in the cell suspension descend to stay near the first outflow port in the filtering device. By the collecting step, the culture medium is caused to flow in the inflow port of the filtering device from the third reservoir, and then the cells staying inside the filtering device flow in the collection vessel with the culture medium from the first outflow port.

(6) Preferably, the control portion brings the culture vessel into a third state in which the first port is located downward relative to the second port by the rotation mechanism or the second rotation mechanism in the moving step.

Due to the fact that the first port is located downward relative to the second port of the culture vessel in the moving step, the cell suspension is easily caused to flow out of the internal space of the culture vessel.

(7) Preferably, the culture vessel has a bag shape in which an internal space is formed with a flexible sheet.

(8) Preferably, an inner surface demarcating the internal space in the culture bag has cell adhesiveness suitable for culturing adhesive cells.

(9) Preferably, the filtration membrane contains hollow fibers.

(10) Preferably, the first pump and the second pump are tube pumps.

(11) A method for concentrating a cell suspension according to the present invention uses a switching mechanism of switching flow passages in a liquid supply circuit connected to a first port bringing the internal space of a culture vessel and the outside into communication with each other, an inflow port bringing an inside of a filtration membrane of a filtering device having a case provided with the filtration membrane in the internal space and an outside of the case into communication with each other, a third port bringing an internal space of a first reservoir and the outside into communication with each other, a fifth port bringing an internal space of a second reservoir capable of reserving a priming liquid in the internal space and the outside into communication with each other, and a sixth port bringing an internal space of a third reservoir capable of reserving a culture medium in the internal space and the outside into communication with each other so that the flow passages are switchable and in a liquid discharge circuit connected to a second port bringing the internal space of the culture vessel and the outside into communication with each other, a first outflow port bringing the inside of the filtration membrane of the filtering device and the outside of the case into communication with each other, a second outflow port bringing the outside of the filtration membrane of the filtering device and the outside into communication with each other, and a fourth port bringing an internal space of the collection vessel and the outside into communication with each other so that the flow passages are switchable, a liquid supply/discharge mechanism having a first pump circulating a liquid in the liquid supply circuit and a second pump circulating a liquid in the liquid discharge circuit, and a rotation mechanism rotating the filtering device so that the positions in the vertical direction of the inflow port and the first outflow port are changeable, and the method includes a moving step of bringing the second port and the third port into communication with each other, and then driving the first pump to thereby move a cell suspension to the first reservoir from the culture vessel, a priming step of bringing the filtering device into a first state in which the inflow port is located downward relative to the first outflow port, bringing the fifth port and the inflow port into communication with each other and opening the inflow port, and then driving at least the first pump drive to thereby supply a priming liquid to the filtering device from the second reservoir, a filtering step of bringing the filtering device into a second state in which the inflow port is located upward relative to the first outflow port, bringing the third port and the inflow port into communication with each other, closing the first outflow port and opening the second outflow port open, and then driving at least the first pump to thereby supply the cell suspension to the filtering device from the first reservoir, and a collecting step of bringing the sixth port and the inflow port into communication with each other, closing the second outflow port and bringing the first outflow port and the fourth port into communication with each other, and then driving at least the first pump to thereby supply the cell suspension to the collection vessel from the filtering device.

ADVANTAGEOUS EFFECTS OF INVENTION

According to the present invention, a cell suspension containing cells cultured in a culture vessel can be simply and efficiently concentrated.

BRIEF DESCRIPTION OF DRAWINGS

FIGS. 5(A) to 5(C) are cross-sectional views illustrating a cut plane V-V of a culture bag 70.

FIG. 18 is a schematic view for explaining the fourth position of the first bag holding portion 31.

DESCRIPTION OF EMBODIMENTS

Hereinafter, a preferable embodiment of the present invention is described. It is a matter of course that this embodiment is merely one embodiment of the present invention and the embodiment can be altered in the range where the scope of the present invention is not altered.

[Outline of Concentrator 10]

Figure 1:
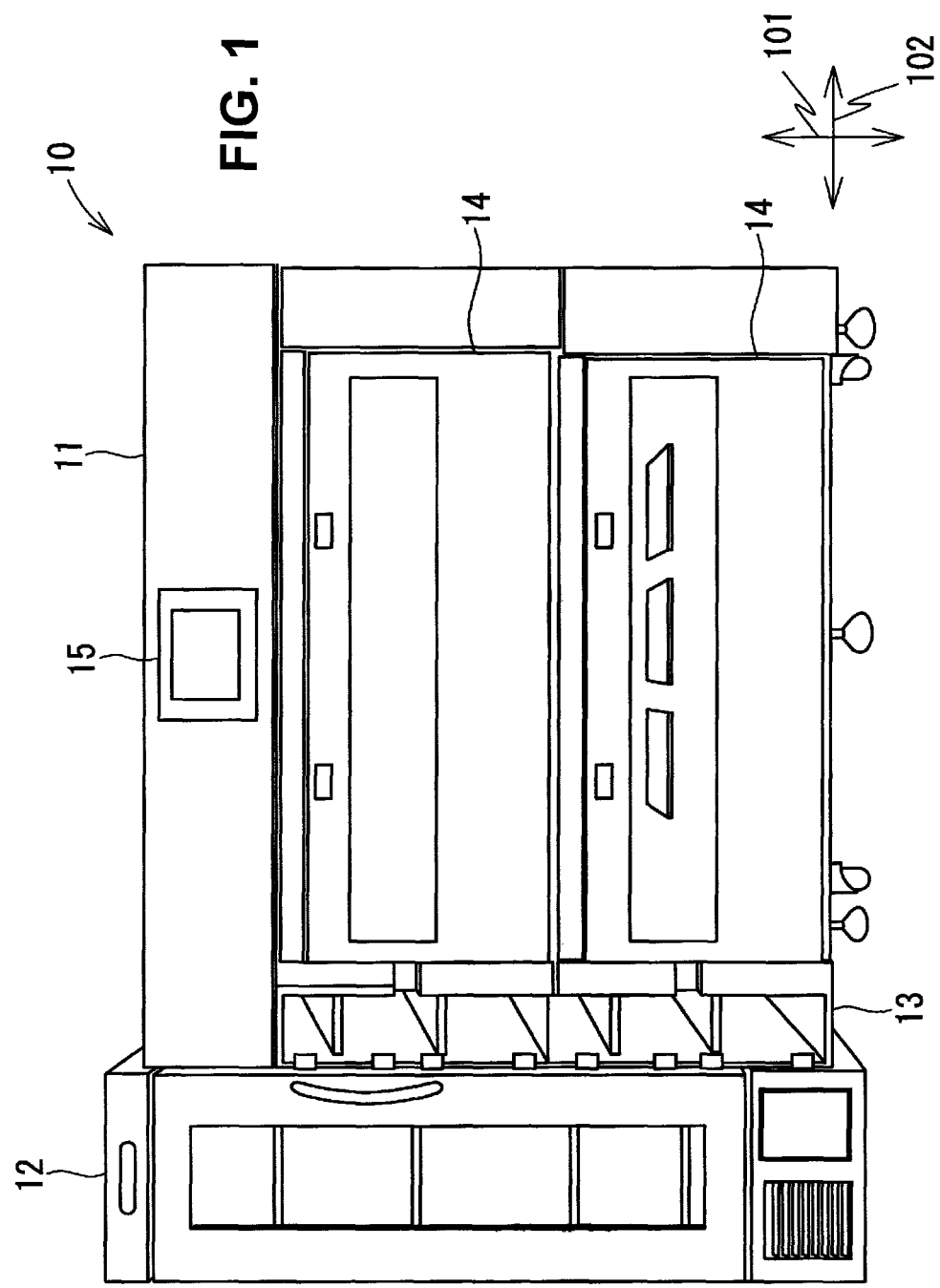
FIG. 1 is a schematic view of a concentrator 10.

As illustrated in FIG. 1, a concentrator 10 has a control portion 11, a cold storage portion 12, a normal temperature storage portion 13, and two culture portions 14. The cold storage portion 12 and the normal temperature storage portion 13 are provided outside the culture portion 14. The two culture portions 14 are separately disposed upward and downward. The control portion 11 has a display 15. The display 15 is disposed on the front surface of the concentrator 10. The control portion 11 has a data input portion (not illustrated), and various conditions about cell culture and the like are input into the control portion 11 through the data input portion.

The concentrator 10 is a device automatically culturing cells according to a program input and stored in the control portion 11. Hereinafter, constituent components of the concentrator 10 are described in detail. In the following description, a vertical direction 101 is defined along the upper and lower sides in FIG. 1, a lateral direction 102 is defined along the right and left sides in FIG. 1, and a forward and backward direction 103 is defined along a direction (direction perpendicular to the sheet surface of FIG. 1) perpendicular to the vertical direction 101 and the lateral direction 102.

Figure 2:
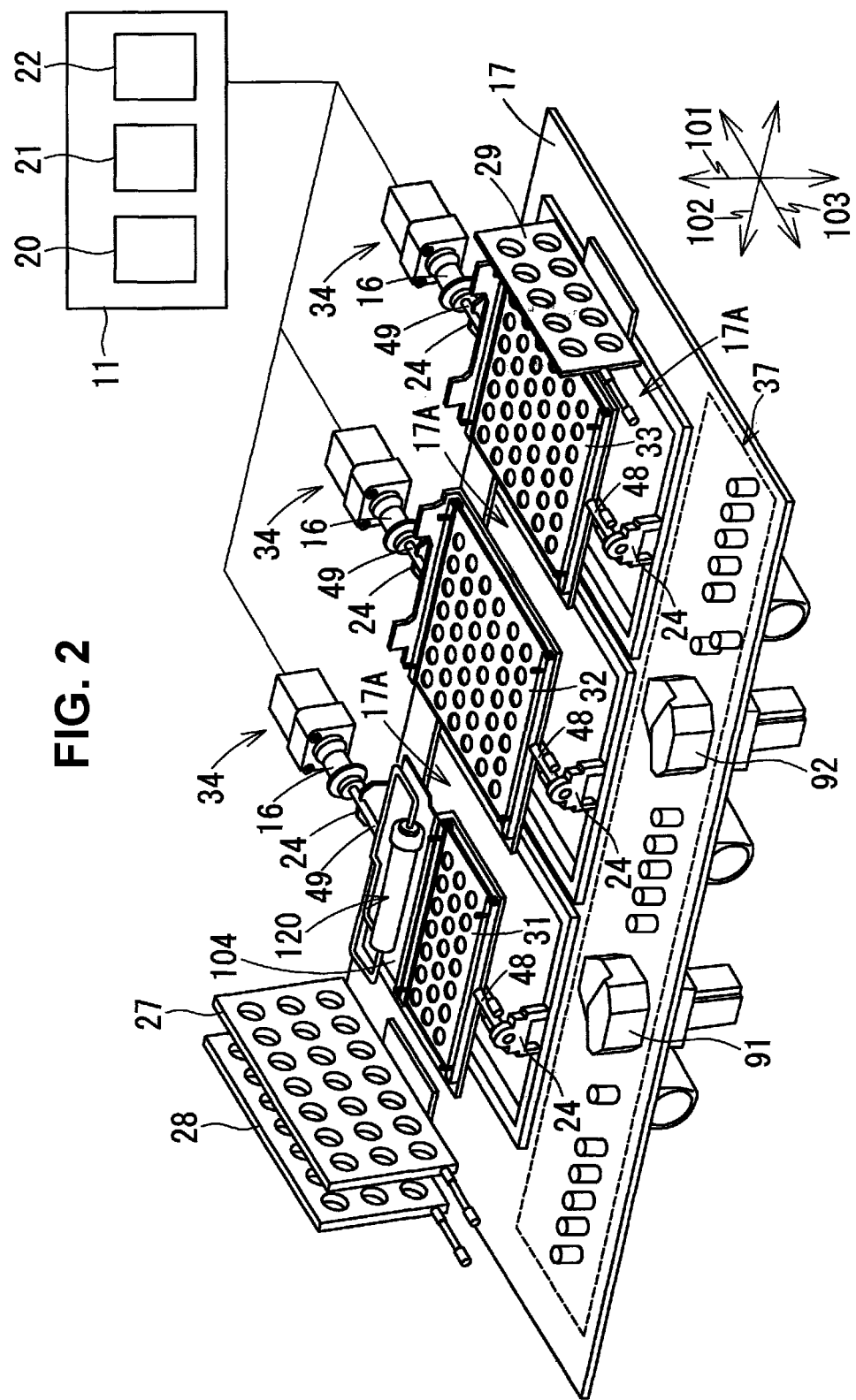
FIG. 2 is a perspective diagram of the inside of a culture portion 14, in which tubes 38 are omitted and a control portion 11 is illustrated for explanation.
Figure 3:
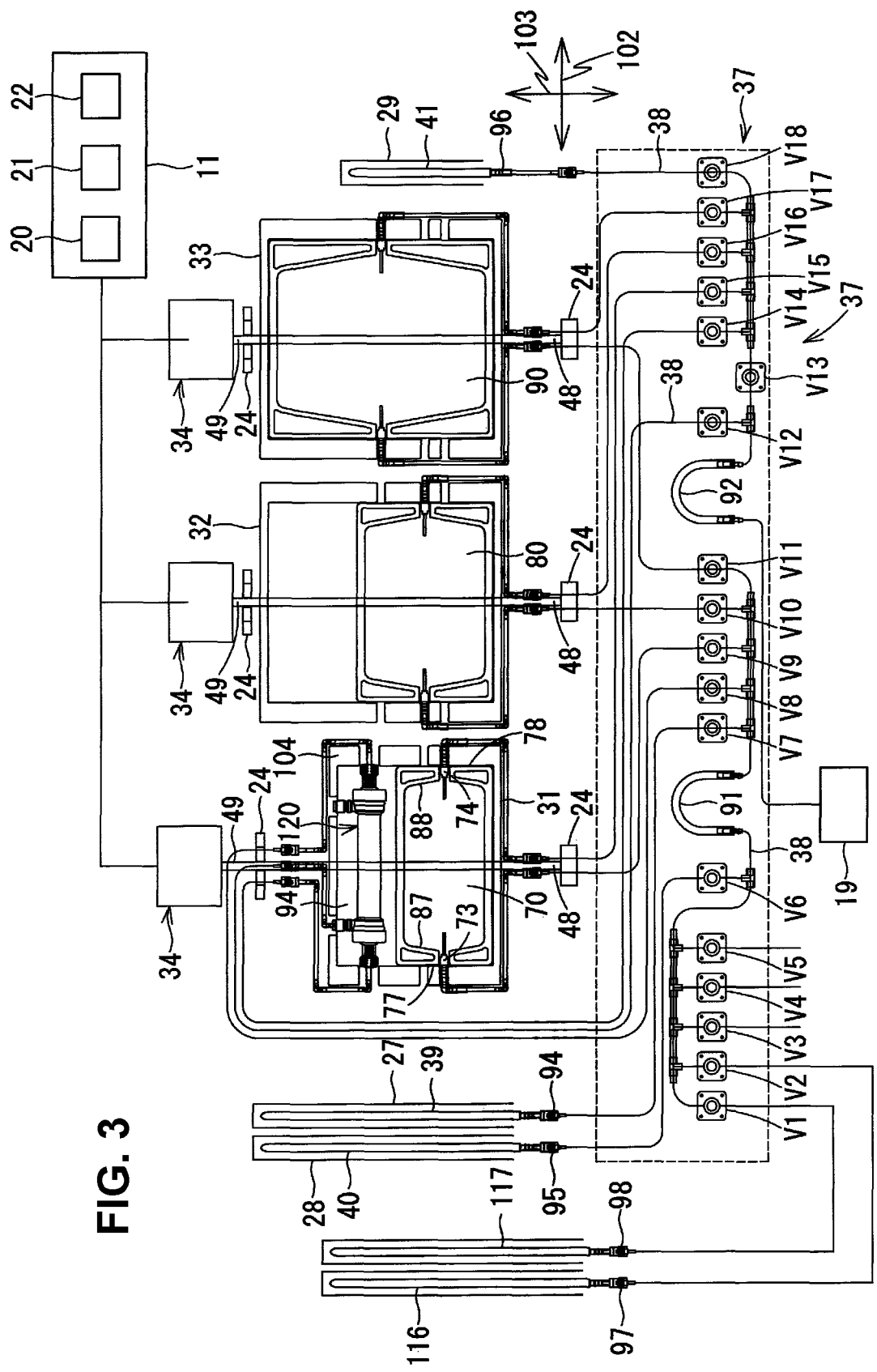
FIG. 3 is a schematic view viewed from above the inside of the culture portion 14, in which holding plates 42 on the upper surface of a first bag holding portion 31, a second bag holding portion 32, and a third bag holding portion 33 are omitted.

As illustrated in FIGS. 2 and 3, the control portion 11 has a rotation control portion 20, a culture control portion 21, and a supply/discharge control portion 22. The rotation control portion 20, the culture control portion 21, and the supply/discharge control portion 22 are arithmetic units for controlling an operation of a control target of each of the portions and store a program and information beforehand. The culture control portion 21 outputs control information to the rotation control portion 20 and the supply/discharge control portion 22. Moreover, the culture control portion 21 outputs control information for controlling the environmental temperature of the culture portions 14. The rotation control portion 20 is electrically connected to the rotation mechanisms 34 and outputs the control information for controlling the drive of the rotation mechanisms 34. The supply/discharge control portion 22 is connected to a liquid supply/discharge mechanism 37 and outputs control information for driving actuators of the liquid supply/discharge mechanism 37, i.e., a supply pump 91, a discharge pump 92, and valves V1 to V18.

As illustrated in FIG. 1, the cold storage portion 12 is a case in which shelfs for placing vessels reserving a reagent or a culture medium therein are formed. On the front surface of the cold storage portion 12, a door capable of opening and closing an opening provided in the front surface of the case is provided. The cold storage portion 12 is a so-called refrigerator having a cooling mechanism (not illustrated). The temperature inside the cold storage portion 12 is kept at an arbitrary preset temperature, e.g., about 10° C. or about 4° C., for example, lower than normal temperature by the cooling mechanism. The normal temperature storage portion 13 is a case having shelves for placing vessels reserving a reagent or a culture medium therein.

The vessels placed inside the cold storage portion 12 and the normal temperature storage portion 13 can reserve a reagent or a culture medium in a fluid tight manner. Examples of the vessels include a bag, a bottle, a cassette, and the like, for example. To each vessel, a tube and the like are connected so that a liquid therein can flow out, and thus a reserved liquid can be caused to flow out by the liquid supply/discharge mechanism 37.

[Culture Portion 14]

The two culture portions 14 have the same structure except a difference in the arrangement in the device, and therefore a detailed configuration thereof is described below taking one culture portion 14 as an example. The culture portion 14 is space formed inside the concentrator 10. The space is partitioned by a case frame of the concentrator 10 and a tray 17 (FIG. 2). The tray 17 can be drawn to the front side from the front surface of the concentrator 10. By drawing of the tray 17, the culture portion 14 is opened, so that each configuration provided in the culture portion 14 can be accessed.

The culture portion 14 can be held at predetermined temperature and $CO_2$ concentration. Although not illustrated in each figure, the culture portion 14 is provided with a warming device and a $CO_2$ supply device. Moreover, the culture portion 14 is provided with a temperature sensor and a $CO_2$ concentration sensor. The culture control portion 21 drives the warming device and the $CO_2$ supply device in order to set the inside of the culture portion 14 to set temperature and $CO_2$ concentration based on outputs of the temperature sensor and the $CO_2$ concentration sensor. In cell culture, the culture portion 14 can be held in an environment of 37° C. and 5% $CO_2$, for example.

As illustrated in FIGS. 2 and 3, the first bag holding portion 31, the second bag holding portion 32, and the third bag holding portion 33 are provided side by side in the lateral direction 102 in the tray 17. The rotation mechanism 34 is provided in the rear side in the forward and backward direction 103 of the first bag holding portion 31. By the rotation mechanism 34, the first bag holding portion 31 is rotated to a predetermined rotation position. Similarly, the rotation mechanism 34 is provided in the rear side in the forward and backward direction 103 of the second bag holding portion 32 and the rotation mechanism 34 is provided in the rear side in the forward and backward direction 103 of the third bag holding portion 33. The liquid supply/discharge mechanism 37 is provided on the front side of the tray 17. Moreover, a filtering device support portion 104 connected to the first bag holding portion 31 in such a manner as to be coaxially rotatable with the first bag holding portion 31 is provided. Moreover, vessel storage portions 27 and 28 are provided on the left side in the lateral direction 102 of the tray 17 and a vessel storage portion 29 is provided on the right side in the lateral direction 102 of the tray 17.

[Third Bag Holding Portion 33]

The first bag holding portion 31, the second bag holding portion 32, and the third bag holding portion 33 basically have the same configuration except a difference in the arrangement and the size, and therefore a detailed configuration is described taking the third bag holding portion 33 as an example. The outer shapes and the sizes of the first bag holding portion 31, the second bag holding portion 32, and the third bag holding portion 33 are designed according to the outer shape of a culture bag which can be held.

Figure 4:
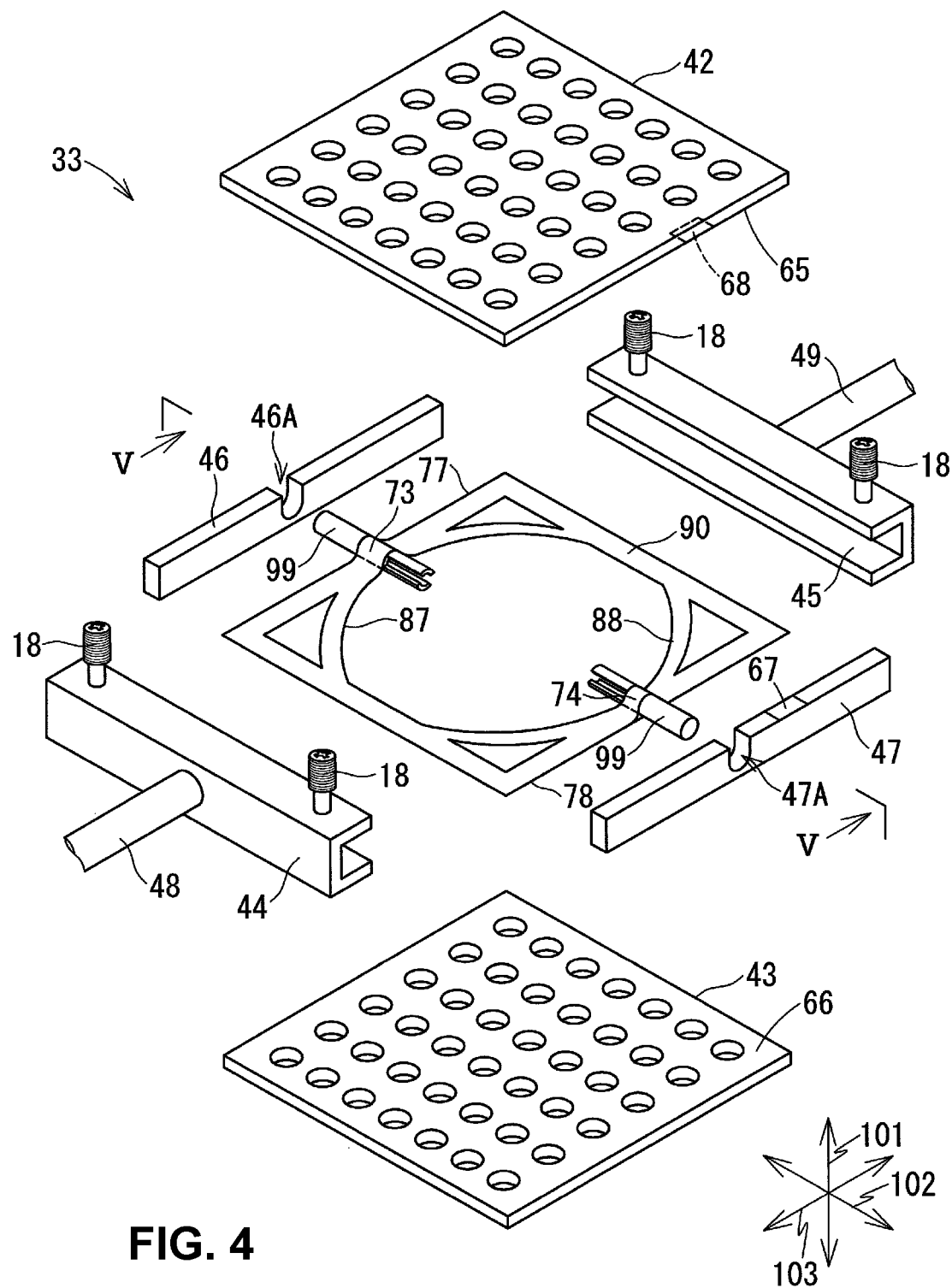
FIG. 4 is an exploded perspective view of the third bag holding portion 33.

As illustrated in FIG. 4 and FIG. 5, the third bag holding portion 33 has holding plates 42 and 43, holders 44 and 45, spacers 46 and 47, and rotating shafts 48 and 49. The holding plates 42 and 43 are rectangular plates. In the holding plates 42 and 43, a plurality of holes penetrating in the thickness direction is formed. The holes increase the heat conduction from gas in the culture portion 14 to the culture bag 90 sandwiched between the holding plates 42 and 43 to be held. The holding plates 42 and 43 are disposed facing each other. The surfaces facing each other in the holding plates 42 and 43 are supporting surfaces 65 and 66.

On the spacer 47, a distance sensor 67 is disposed. On the holding plate 42 abutting on the spacer 47, a magnet 68 is disposed facing the distance sensor 67. The distance sensor 67 outputs a voltage according to the magnetic flux density from the magnet 68, and a hall element is used, for example. When the holding plates 42 and 43 are in a usual state of holding a culture bag, the distance between the holding plate 42 and the spacer 47 is constant, and therefore an output of the distance sensor 67 is also constant. When the holding plates 42 and 43 are bent in such a manner as to be spread out in a direction where the holding plates 42 and 43 are separated from each other due to the fact that the amount of a liquid flowing into the culture bag is large and a culture bag is expanded, resulting in an increase in the distance between the holding plate 42 and the spacer 47, the magnetic flux density of the magnet 68 which the distance sensor 67 detects decreases, and the output of the distance sensor 67 varies.

The control portion 11 stores a threshold value beforehand. The threshold value is a value for judging that the distance between the holding plate 42 and the spacer 47 increases to reach a fixed value or above. The control portion 11 can judge that the distance between the holding plate 42 and the spacer 47 increases to reach a fixed value or above by comparing an output of the distance sensor 67 with the threshold value. The distance sensor 67 may be provided in the spacer 46 instead of the spacer 47 or may be provided in both the spacers 46 and 47. The magnet 68 may be provided in either the holding plate 42 or 43 insofar as the magnetic flux is detectable by the distance sensor 67. The arrangements of the distance sensor 67 and the magnet 68 are relative. It is a matter of course that the arrangement of the distance sensor 67 and the arrangement of the magnet 68 may be switched. The distance sensor 67 and the magnet 68 may be disposed facing each other in the holding plates 42 and 43.

The spacers 46 and 47 are disposed in a pair of edge portions facing each other which are located between the holding plates 42 and 43 and in which ports 73 and 74 of the culture bag 90 (an example of the culture vessel) are disposed. The spacers 46 and 47 maintain the interval between the holding plates 42 and 43. The spacers 46 and 47 each have a square pole shape. The length in the longitudinal direction of the spacers 46 and 47 is almost the same as the length of the pair of edge portions of the holding plates 42 and 43. The cross-sectional shape of the spacers 46 and 47 is fixed over a longitudinal direction. In the center in the longitudinal direction of the spacers 46 and 47, recessed portions 46A and 47A recessed in a direction orthogonal to the longitudinal direction are formed. The recessed portions 46A and 47A are space into which tubes 99 of the culture bag 90 each are inserted. The spacers 46 and 47 may be integrally configured with one of the holding plates 42 and 43.

The holders 44 and 45 sandwich the holding plates 42 and 43 in a state where the spacers 46 and 47 are present therebetween to integrally hold the same. The holders 44 and 45 are long and narrow members having a cross section of a lateral U-shape. Into the inside of the lateral U-shape, edge portions of the holding plates 42 and 43 in the state where the spacers 46 and 47 are present therebetween are inserted. The edge portions of the holding plates 42 and 43 to be inserted into the holders 44 and 45 are a pair of edge portions where the spacers 46 and 47 are not present. On both end sides in the longitudinal direction of each of the holders 44 and 45, screw holes are formed, and screws 18 are screwed into the screw holes. The tip of the screws 18 is projected to the inside of the lateral U-shape of the holders 44 and 45. Due to the fact that one of the holders 44 and 45 inserted into the lateral U-shape of the holders 44 and 45 is pressurized by the screws 18, the holders 44 and 45 hold the holding plates 42 and 43 in the state where the spacers 46 and 47 are present therebetween. In this state, space formed between the supporting surfaces 65 and 66 of the holding plates 42 and 43 serves as space holding a culture bag. The holders 44 and 45 may be integrally configured with one of the holding plates 42 and 43. The holding plates 42 and 43 may be turnably connected by one of the holders 44 and 45 as in a hinge.

The holders 44 and 45 are provided with rotating shafts 48 and 49, respectively, which are projected from the vicinity of the center in the longitudinal direction to the side opposite to the side where the holding plates 42 and 43 are held. The rotating shafts 48 and 49 coaxially extend in the state where the holders 44 and 45 hold the holding plates 42 and 43. The direction where the rotating shafts 48 and 49 extend is in parallel to the supporting surfaces 65 and 66 of the holding plates 42 and 43.

As illustrated in FIG. 5(A), in the case where a liquid is not contained in the culture bag 90 supported by the third bag holding portion 33 when the third bag holding portion 33 is in a state where the supporting surface 66 is located downward relative to the supporting surface 65 and the supporting surfaces 65 and 66 are in parallel with the horizontal direction, the culture bag 90 mainly contacts the supporting surface 66. Herein, the distance between the supporting surfaces 65 and 66 is a distance D1. As illustrated in FIG. 5(B), even when it is supposed that the culture bag 90 expands by a reserved liquid to contact the supporting surfaces 65 and 66, a liquid of a capacity with which the holding plates 42 and 43 are not bent is caused to flow in the culture bag 90. Such a liquid amount is set as the amount of a liquid which can be reserved in the culture bag 90 beforehand. As illustrated in FIG. 5(C), when a liquid with an amount larger than the preset amount is caused to flow in the culture bag 90, the culture bag 90 in contact with the supporting surfaces 65 and 66 further expands to bend the holding plates 42 and 43 in such a manner as to be spread out in a direction of separating from each other. Due to the bending of the holding plates 42 and 43, the distance between the supporting surfaces 65 and 66 increases (Distance D2). When a detection value of the distance sensor 67 according to the distance between the holding plate 42 and the spacer 47 exceeds the threshold value described above, the control portion 11 judges that the distance between the supporting surfaces 65 and 66 exceeds the distance D2.

Detailed configurations of the first bag holding portion 31 and the second bag holding portion 32 are not described in detail with reference to the drawings but have holding plate holders and spacers as with the third bag holding portion 33.

[Filtering Device Support Portion 104]

Figure 6:
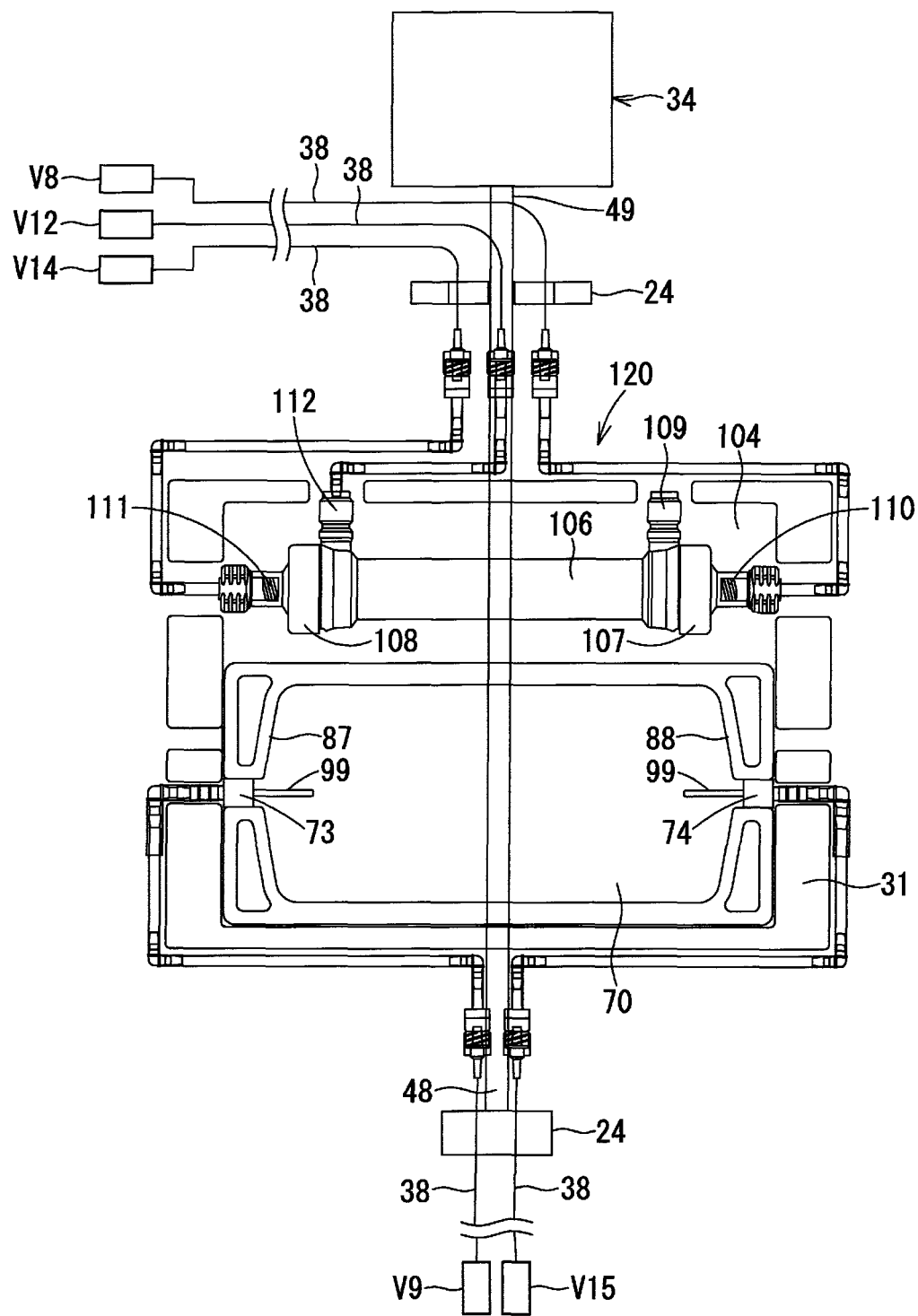
FIG. 6 is a schematic view of the first bag holding portion 31 for explaining a filtering device 120.

As illustrated in FIG. 6, a filtering device support portion 104 is disposed in the rear side in the forward and backward direction 103 of the first bag holding portion 31. The filtering device support portion 104 is integrally connected to the first bag holding portion 31. Therefore, the filtering device support portion 104 rotates integrally with the first bag holding portion 31 around the rotating shafts 48 and 49. The filtering device support portion 104 supports a filtering device 120. The filtering device 120 supported by the filtering device support portion 104 is disposed so that an inflow port 110 and a first outflow port 111 each face a direction crossing (in this embodiment, direction orthogonal to) the rotation axis by the rotating shafts 48 and 49. Thus, when the filtering device 120 rotates around the rotating shafts 48 and 49 with the filtering device support portion 104, the positions in the vertical direction 101 of the inflow port 110 and the first outflow port 111 are changed. A direction where each of the inflow port 110 and the first outflow port 111 of the filtering device 120 supported by the filtering device support portion 104 extends and a direction where each of the ports 73 and 74 of a culture bag 70 held by the first bag holding portion 31 extends are in agreement with each other.

As illustrated in FIG. 2, openings 17A are formed in three places in the tray 17 in the portions where the first bag holding portion 31, the second bag holding portion 32, the third bag holding portion 33, and the filtering device support portion 104 are disposed in order to avoid interference with the first bag holding portion 31, the second bag holding portion 32, the third bag holding portion 33, and the filtering device support portion 104 which are rotating.

In the front side and the rear side in the forward and backward direction 103 of each opening 17A, a pair of bearing portions 24 is individually disposed. The pair of bearing portions 24 rotatably supports each of the rotating shafts 48 and 49 of the first bag holding portion 31, the second bag holding portion 32, the third bag holding portion 33, and the filtering device support portion 104 in the state in parallel with the forward and backward direction 103. Thus, each of the holding plates 42 and 43 of the first bag holding portion 31, the second bag holding portion 32, and the third bag holding portion 33 and the filtering device support portion 104 can be rotated around the rotating shafts 48 and 49 as the rotation center.

Figure 8:
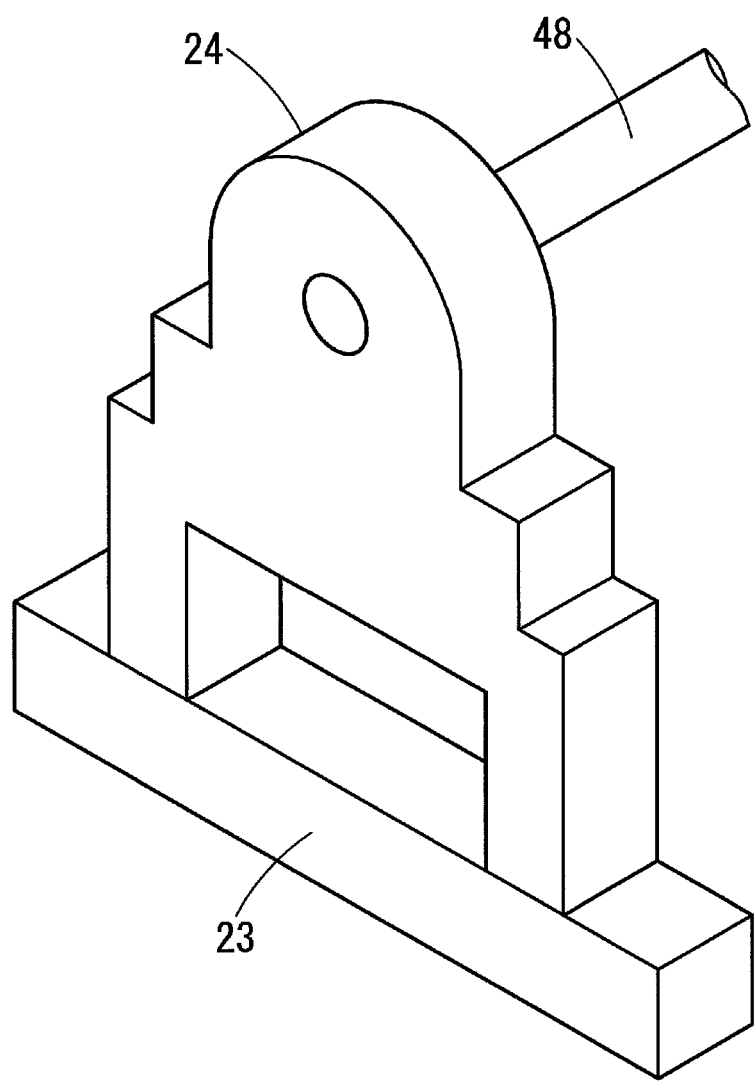
FIG. 8 is a perspective diagram of a weight detector 23 and a bearing portion 24.

As illustrated in FIG. 8, each bearing portion 24 is placed on each weight detector 23 provided on the tray 17. By a pair of weight detectors 23 corresponding to each of the first bag holding portion 31, the second bag holding portion 32, or the third bag holding portion 33, the weights of the corresponding bag holding portion, a culture bag held by the corresponding bag holding portion, the bearing portion 24, and the like are detected. As the weight detector 23, a load cell converting power (weight) applied to the weight detector 23 to an electric signal or the like is used, for example.

[Rotation Mechanism 34]

As illustrated in FIG. 2 and FIG. 3, the rotation mechanism 34 is provided in the rear side in the forward and backward direction 103 of each bearing portion 24 in the tray 17. The rotation mechanism 34 has a rotation shaft support portion 16 and a stepping motor (not illustrated). The rotation shaft support portion 16 extends toward the rear side in the forward and backward direction 103 and is coaxially connected to the rotating shaft 49 supported by each bearing portion 24. Although not illustrated in each figure, power is supplied to the stepping motor from a power supply. Moreover, drive is transmitted to the stepping motor and the rotation shaft support portion 16 by a known speed reduction gear or the like. By the supply of power based on a control signal output from the rotation control portion 20 to the stepping motor, the rotation shaft support portion 16 rotates by only a predetermined rotation angle. The stepping motor may be provided with a sensor for detecting the original point position, i.e., the rotation position where the supporting surfaces 65 and 66 of the holding plates 42 and 43 of the first bag holding portion 31, the second bag holding portion 32, and the third bag holding portion 33 are in parallel with the horizontal direction. The rotation control portion 20 can drive the stepping motor so that the supporting surfaces 65 and 66 are in parallel with the horizontal direction based on the output of this sensor. Similarly, the stepping motor can be driven so that the inflow port 110 and the first outflow port 111 of the filtering device 120 extend in the horizontal direction. The stepping motor is an example of a driving source of the rotation mechanism 34 and the other driving sources, such as a DC motor having an encoder capable of detecting the rotation amount, may be used, for example, in replace of the stepping motor. The rotation position of the driving source may be detected by other detection means, such as a resolver, or a sensor capable of directly detecting the rotation position of the first bag holding portion 31 and the like may be provided.

[Liquid Supply/Discharge Mechanism 37]

As illustrated in FIGS. 2 and 3, the liquid supply/discharge mechanism 37 has a supply pump 91, a discharge pump 92, and a plurality of valves V1 to V18. As the supply pump 91 and the discharge pump 92, known substances capable of sending a liquid in a tube are used. Examples of such a pump include a so-called tube pump sending liquid by squeezing an elastic tube with a turning roller, for example. Power is supplied to the supply pump 91 and the discharge pump 92 from the power supply. The supply/discharge control portion 22 can drive the supply pump 91 and the discharge pump 92 for a definite period of time by controlling the power supplied to the supply pump 91 and the discharge pump 92.

The plurality of valves V1 to V18 are roughly classified into the valves V1 to V11 relating to the supply pump 91 and the valves V12 to V18 relating to the discharge pump 92. The supply pump 91 and the valves V1 to V11 are a liquid supply mechanism 81 in the liquid supply/discharge mechanism. 37 and the discharge pump 92 and the valves V12 to V18 are a liquid discharge mechanism 82 in the liquid supply/discharge mechanism 37. In each valve V1 to V18, ON/OFF is switched based on a control signal output from the supply/discharge control portion 22. By ON/OFF of each valve V1 to V18, the flow of a liquid in each tube 38 connected to the culture bag and the like can be changed. The valves V1 to V18 are examples of the switching mechanism. As the valves V1 to V18, an electromagnetic valve is used, for example.

[Culture Circuit]

As illustrated in FIG. 3, a culture circuit has three culture bags 70, 80, and 90, two server bags 39 and 40 (one example of the first reservoir), a collection bag 41 (one example of the collection vessel), the filtering device 120, reservoirs 116 and 117 (one example of the second reservoir and the third reservoir) held by the cold storage portion 12 or the normal temperature storage portion 13, and a plurality of tubes 38 connecting them so that a liquid can flow. The culture bag 70 is disposed in the first bag holding portion 31. The culture bag 80 is disposed in the second bag holding portion 32. The culture bag 90 is disposed in the third bag holding portion 33. The filtering device 120 is disposed in the filtering device support portion 104. The collection bag 41 is disposed in the culture portion 14. The culture bags 70, 80, and 90 have the same configuration except that the capacity of the culture bag 70 is smaller than that of the culture bags 80 and 90, and therefore a detailed configuration is described below taking the culture bag 90 as an example.

Figure 9A:
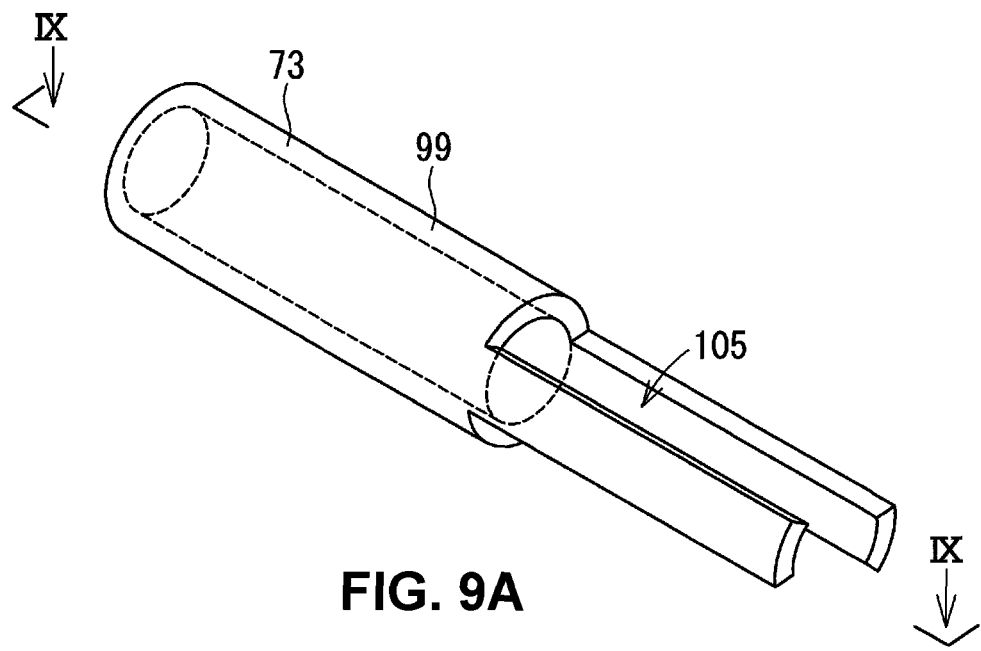
FIG. 9(A) is a perspective diagram of a tube 99 and FIG. 9(B) is a schematic view of a cross section along a cut plane IX-IX of the tube 99.
Figure 9B:
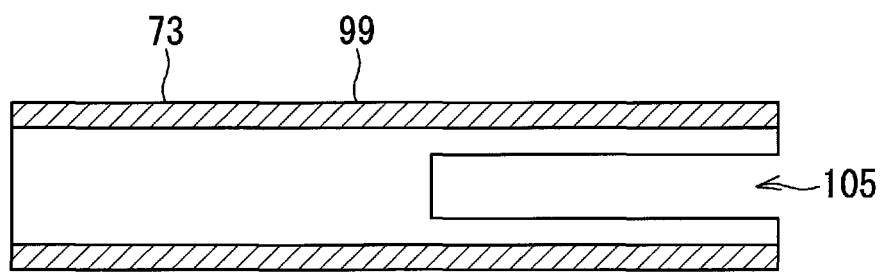
Figure 10:
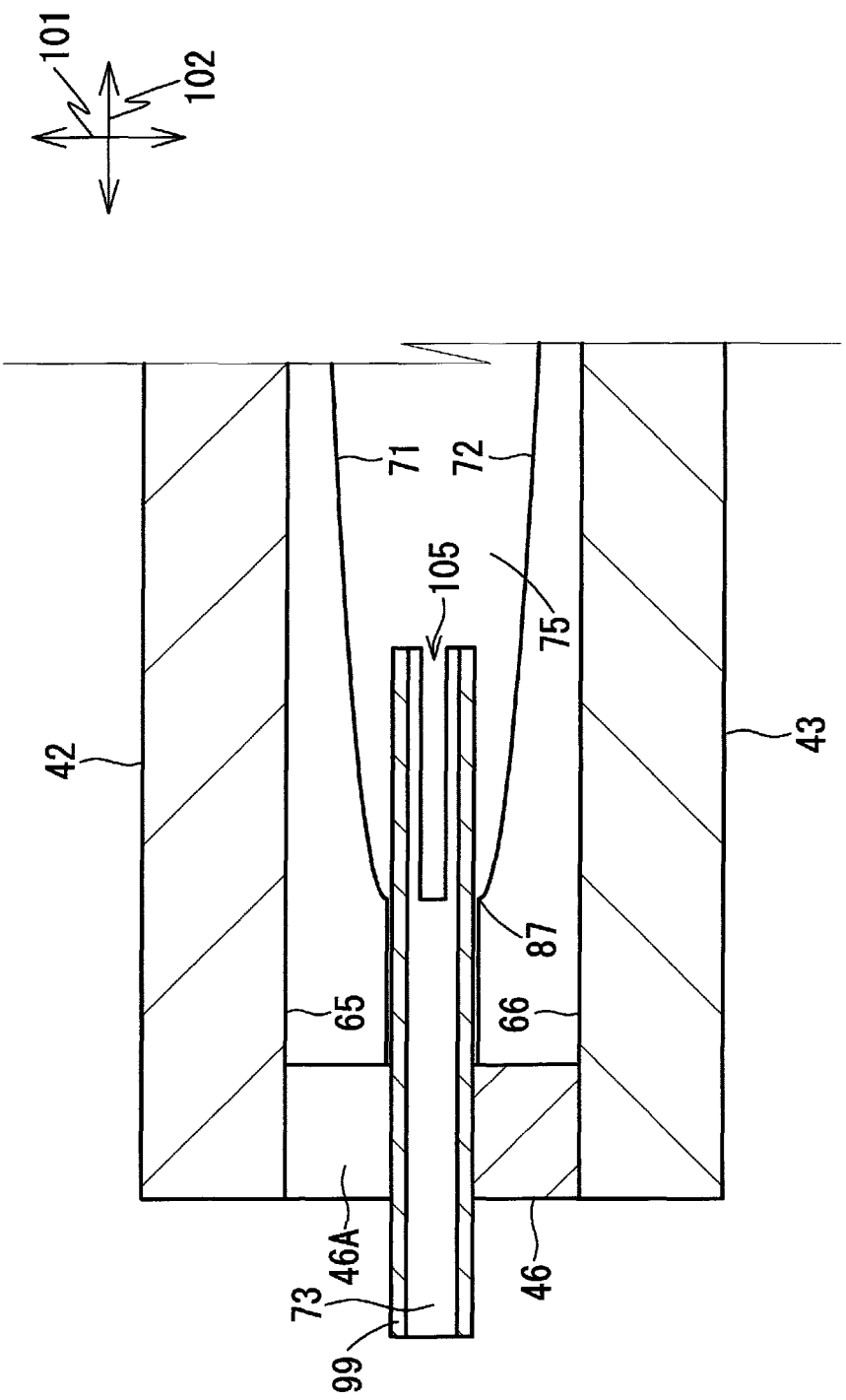
FIG. 10 is an enlarged cross-sectional view illustrating a cut plane V-V of the culture bag 70.

As illustrated in FIG. 4, the culture bag 90 is formed into a bag shape by bonding peripheral edges of two rectangular sheets formed of a synthetic resin by known methods, such as thermal welding. The tubes 99 formed of a synthetic resin are disposed near the center of each of a pair of end portions 77 and 78 facing each other in the two rectangular sheets. In a portion located in an internal space 75 of the culture bag 90 of each tube 99, a notch portion 105 is formed toward edges 87 and 88 from the ends located in the internal space 75 of the culture bag 90 as illustrated in FIGS. 9(A) and 9(B). The notch portion 105 is located in a portion not facing inner surfaces 71 and 72 demarcating the internal space 75 of the culture bag 90, i.e., a place facing end portions other than the pair of end portions 77 and 78 in the two rectangular sheets, as illustrated in FIG. 10. Even when it is supposed that, when a liquid is caused to flow out of the culture bag 90, the inner surfaces 71 and 72 are brought close to each other by a negative pressure arising in the internal space 75, the inner surfaces 71 and 72 are difficult to contact each other near the tubes 99 due to the fact that the tubes 99 are present between the inner surfaces 71 and 72. On the other hand, since the notch portion 105 is formed in a place not facing the inner surfaces 71 and 72 in the tubes 99, a liquid remaining near the edges 87 and 88 of the internal space 75 can flow in the internal space of the tubes 99 through the notch portions 105.

As illustrated in FIG. 4, the internal space 75 of the culture bag 90 is brought into communication with the outside through the internal space of the tubes 99. More specifically, the ports 73 and 74 are formed by the tubes 99. The edges 87 and 88 where the tubes 99 are disposed of the edges demarcating the internal space 75 of the culture bag 90 have a tapered shape in which the distance between the edges 87 and 88 decreases as separating from the ports 73 and 74. In other words, the edges 87 and 88 have a shape of expanding to the outside of the culture bag 90 toward the center where the tubes 99 are disposed. In the state where the culture bag 90 is held by the first bag holding portion 31, the tubes 99 extend in a direction orthogonal to the rotating shafts 48 and 49. More specifically, the ports 73 and 74 extend in the direction orthogonal to the rotating shafts 48 and 49.

The synthetic resin sheet for use in the culture bag 90 has flexibility and has bending rigidity with which the bag shape can be maintained when a culture medium is placed therein. For example, low density polyethylene, ultrahigh molecular weight polyethylene, cyclic polyolefin resin, and those having a laminated structure with the materials above or other materials are mentioned.

The inner surfaces 71 and 72 of the culture bag 90 have cell adhesiveness suitable for culturing adhesive cells. In detail, cell adhesive functional groups are exposed by plasma treatment or the like, for example, in the inner surfaces 71 and 72. Examples of the cell adhesive functional group include an amino group, an amine group, a hydroxyl group, a sulfone group, a sulfen group, a sulfin group, an ether group, a carboxyl group, a carbonyl group, and the like, for example. Among the above, an amino group and a carboxyl group having high adhesiveness with cells are preferable.

The server bags 39 and 40, the collection bag 41, and the reservoirs 116 and 117 illustrated in FIG. 3 are formed into a bag shape by bonding synthetic resin sheets and have at least one of ports 94 to 98 (one example of the third port, the fourth port, the fifth port, and the sixth port). The server bags 39 and 40 reserve a culture medium. The collection bag 41 collects a cell suspension. The reservoirs 116 and 117 reserve a peeling liquid and a priming liquid. For the server bags 39 and 40, the collection bag 41, and the reservoirs 116 and 117, known vessels capable of reserving a culture medium and a cell suspension are usable besides known bags.

As illustrated in FIG. 3, tubes 38 are individually connected to each port of the culture bags 70, 80, and 90, the server bags 39 and 40, the collection bag 41, and the reservoirs 116 and 117. Each tube 38 connected to one port 73 of each of the culture bags 70, 80, and 90, the tube 38 connected to the inflow port 110 of the filtering device 120, each tube 38 connected to each of the ports 94 and 95 of the server bags 39 and 40, and each tube 38 connected to each of the ports 97 and 98 of the reservoirs 116 and 117 is extended to the supply pump 91. These tubes 38 are integrated into one tube 38 through a connector before reaching the supply pump 91 to configure a liquid supply circuit. Moreover, the tubes 38 each are passed through the valves V6 to V11 before integrated into one tube 38 and the valves V6 to V11 can change the internal space of each tube 38 to an opened state where a liquid can flow and a closed state where a liquid cannot flow.

Each tube 38 connected to the other port 74 of each of the culture bags 70, 80, and 90, each tube 38 connected to the first outflow port 111 and a second outflow port 112 of the filtering device 120, and the tube 38 connected to the port 96 of the collection bag 41 are extended to the discharge pump 92. These tubes 38 are integrated into one tube 38 before reaching the discharge pump 92 through a connector to configure a liquid discharge circuit. Moreover, the tubes 38 each are passed through the valves V12 and V14 to V18 before integrated into one tube 38 and the valves V12 and V14 to V18 can change the internal space of each tube 38 to an opened state where a liquid can flow and a closed state where a liquid cannot flow.

The tube 38 leading to the supply pump 91 is branched again, and then each tube 38 is connected to bags and vessels placed in the cold storage portion 12 or the normal temperature storage portion 13 through the valves V1 to V5. These bags and the vessels reserve a cell suspension, a culture medium, a peeling liquid, and the like. The tube 38 leading to the discharge pump 92 is connected to a waste liquid vessel 19.

[Filtering Device 120]

Figure 7:
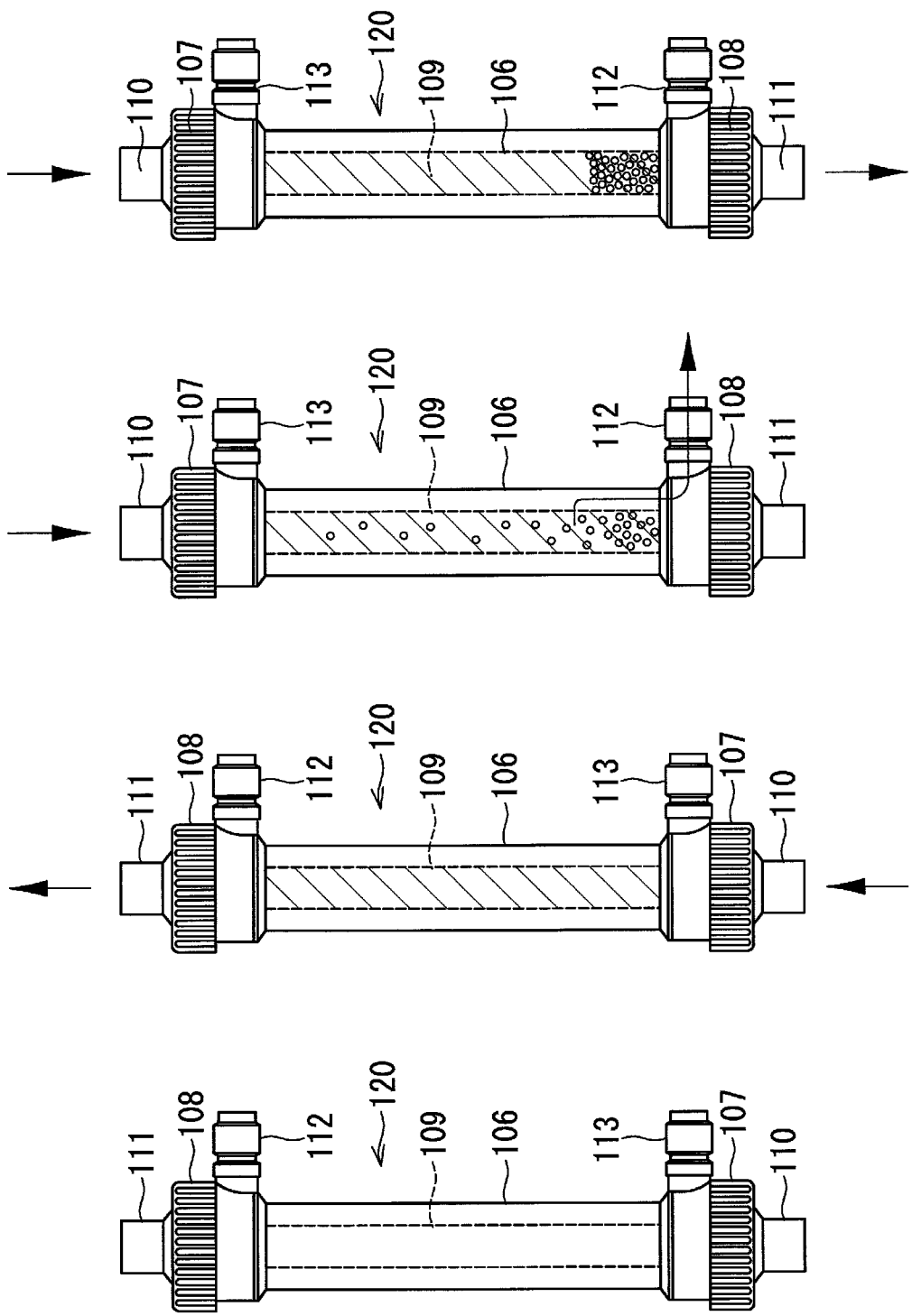
FIGS. 7(A) to 7(D) are schematic views of the filtering device 120.

As illustrated in FIG. 7(A), the filtering device 120 has a body 106 (one example of the case), a cap 107, a cap 108, and a hollow fiber bundle 109 (one example of the filtration membrane). The body 106 has an approximately cylindrical shape. The body 106 is opened in both sides in the axial direction (direction along the vertical direction in FIG. 7(A)). The cap 107 and the cap 108 are screwed into each opening of the body 106. In the cap 107, the inflow port 110 bringing the internal space and the external space of the filtering device 120 into communication with each other is formed so as to extend along the axial direction of the body 106. In the cap 108, the first outflow port 111 bringing the internal space and the external space of the filtering device 120 into communication with each other is formed so as to extend along the axial direction of the body 106.

A pair of hollow fiber supports (not illustrated) is formed near each opening of the body 106. The hollow fiber bundle 109 is supported by the pair of hollow fiber supports to be disposed in the internal space of the body 106. Both ends of the hollow fiber bundle 109 are disposed near the openings of the body 106. The hollow fiber supports support both the ends of the hollow fiber bundle 109 and separates both the ends of the hollow fiber bundle 109 and the internal space of the body 106 in a fluid tight manner. Therefore, a liquid flowing into the internal space of the body 106 through the inflow port 110 of the cap 107 flows into one end of a hollow fiber bundle 114 and does not flow in the space demarcated by the pair of hollow fiber supports in the internal space of the body 106. On the other hand, a liquid flowing out of the other end of the hollow fiber bundle 109 flows out of the first outflow port 111 of the cap 108 to the outside and a liquid does not flow in the first outflow port 111 from the space demarcated by the pair of hollow fiber supports in the internal space of the body 106.

In the body 106, the second outflow port 112 extends in a direction orthogonal to the axial direction (direction along the vertical direction in FIG. 7) of the body 106 on the side where the cap 108 is screwed and the port 113 extends in a direction orthogonal to the axial direction of the body 106 on the side where the cap 107 is screwed. The second outflow port 112 and the port 113 bring the space demarcated by the pair of hollow fiber supports in the internal space of the body 106 and the outside of the body 106 into communication with each other. A liquid flowing out of the hollow fiber bundle 109 by filtering is caused to flow out to the outside through the second discharge port 112. The port 113 is sealed in this embodiment. The tubes 38 described above are connected to the inflow port 110, the first outflow port 111, and the second outflow port 112.

The hollow fiber bundle 109 is a bundle of hollow fibers in which a dialysis membrane is formed into a tubular shape. The hollow fibers each are opened in both ends thereof. Examples of raw materials of the hollow fibers include triacetate, polyether sulfone, and the like. The thickness, film thickness, pore size, length, type, and the like of the hollow fibers are set as appropriate according to the conditions, such as a size, of cells to be filtered in the filtering device 120.

[Cell Culture Method Using Concentrator 10]

Hereinafter, a cell culture method using the concentrator 10 is described. The cell culture using the concentrator 10 can be performed by arbitrarily selecting any one or a plurality of the culture bags 70, 80, and 90 but, hereinafter, a cell culture method using only the culture bag 70 is described. The cell culture method using the concentrator 10 includes each step described below.

(1) Culture step of amplifying cells in the culture bag 70.

(2) Culture medium exchanging step of exchanging culture media in the culture bag 70.

(3) Cell suspension collecting step of collecting a cell suspension in the culture bag 70.

(4) Cell suspension concentrating step of concentrating a cell suspension in the server bag 40.

In the concentrator 10, a culture circuit is set beforehand. In detail, as illustrated in FIG. 3, the culture bags 70, 80, and 90 are set in the first bag holding portion 31, the second bag holding portion 32, and the third bag holding portion 33, respectively, the filtering device 120 is set in the filtering device support portion 104, the server bags 39 and 40 are held by the vessel storage portions 27 and 28, respectively, and the collection bag 41 is held by the vessel storage portion 29. The reservoirs 116 and 117 are held by the cold storage portion 12 or the normal temperature storage portion 13. The tubes 38 of the circuit are set in the valves V1 to V18, the supply pump 91, and the discharge pump 92.

A user sets beforehand the culture control portion 21 so that the culture step, the culture medium exchanging step, the culture step, the cell suspension concentrating step, and the cell suspension collecting step are successively performed. A user also sets beforehand various settings, such as the culture time in the culture step, the culture medium exchange amount in the culture medium exchanging step, the concentration time and the culture medium supply amount in the cell suspension concentrating step, and the reaction time with a peeling liquid in the cell suspension collecting step. The culture control portion 21 outputs a first information containing various setting information in the culture step, outputs a second information containing various setting information in the culture medium exchanging step, and outputs a third information containing various setting information in the cell suspension collecting step. The culture control portion 21 outputs various setting information in the cell suspension concentrating step. The rotation control portion 20 controls the drive of the rotation mechanism 34 based on each information output from the culture control portion 21. The supply/discharge control portion 22 controls the drive of the liquid supply/discharge mechanism 37 (liquid supply mechanism 81 and liquid discharge mechanism 82) based on each information output from the culture control portion 21.

Figure 11:
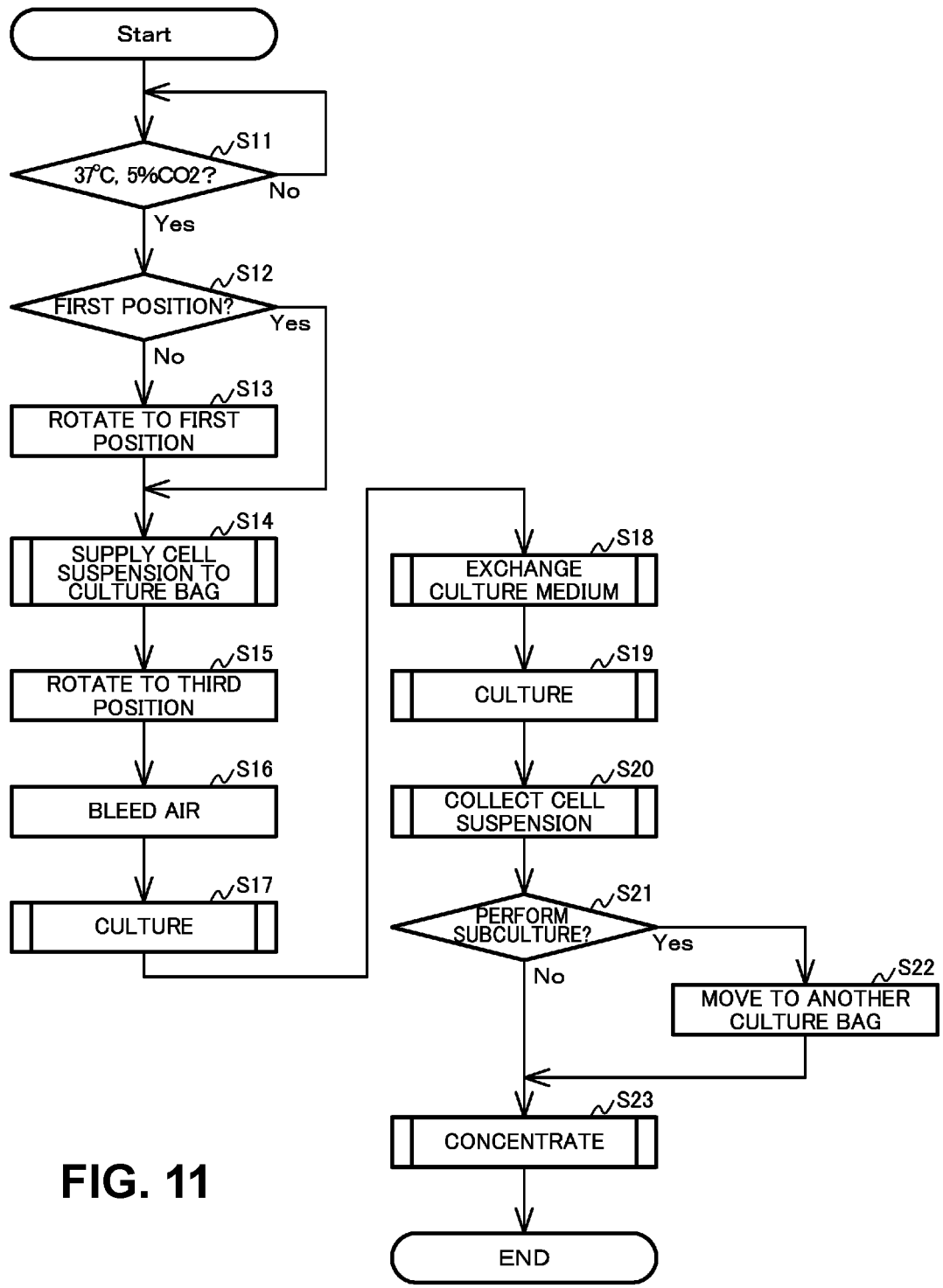
FIG. 11 is a flow chart of a cell culture method.
Figure 12:
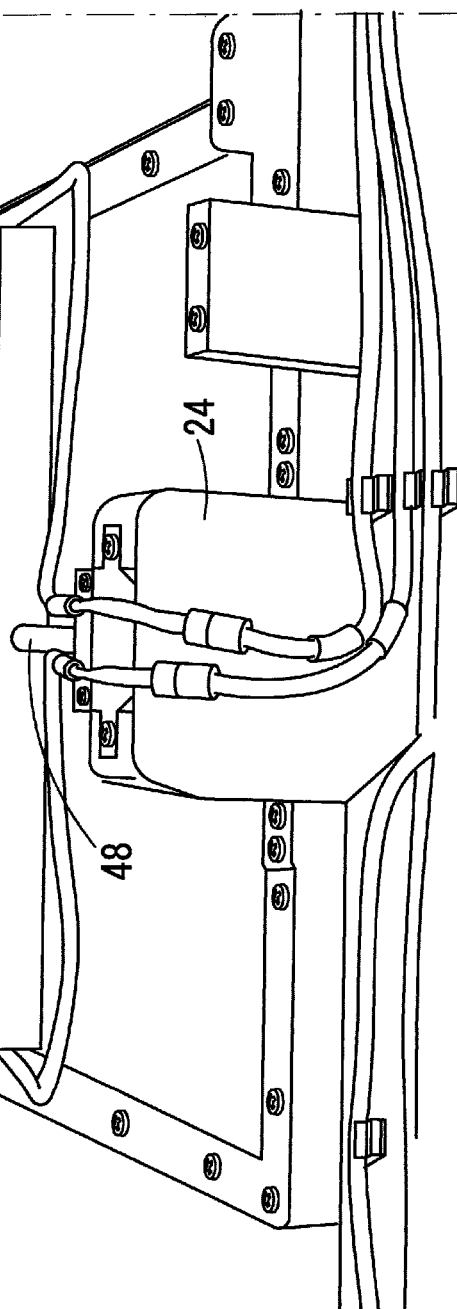
FIG. 12 is a schematic view for explaining a first position of the first bag holding portion 31.

As illustrated in FIG. 11, the culture portion 14 in the concentrator 10 performs a preliminary operation due to the fact that the culture control portion 21 receives an input of start of culture. In detail, due to the fact that the warming device and the $CO_2$ supply device are driven based on the control information from the culture control portion 21, the temperature of the culture portion 14 is adjusted to 37° C. and the carbon dioxide concentration is adjusted to 5% (Step S11). Subsequently, the rotation control portion 20 judges whether the first bag holding portion 31 is in the first position (Step S12). When the rotation control portion 20 judges that the first bag holding portion 31 is not in the first position, i.e., the stepping motor in the rotation mechanism 34 is not located at the original point position (Step S12: No), the rotation control portion 20 rotates the stepping motor of the rotation mechanism 34 until the stepping motor reaches the original point position. Thus, as illustrated in FIG. 12, the first bag holding portion 31 stops at the first position in which the supporting surfaces 65 and 66 are in parallel with the horizontal direction (Step S13). When the first bag holding portion 31 is in the first position (Step S12: Yes), the rotation control portion 20 does not drive the rotation mechanism 34. The supporting surfaces 65 and 66 in the first position may be almost in parallel with the horizontal direction and do not need to be strictly in parallel with the horizontal direction. The valves V1 to V18 bring the tubes 38 into the closed state.

Figure 13:
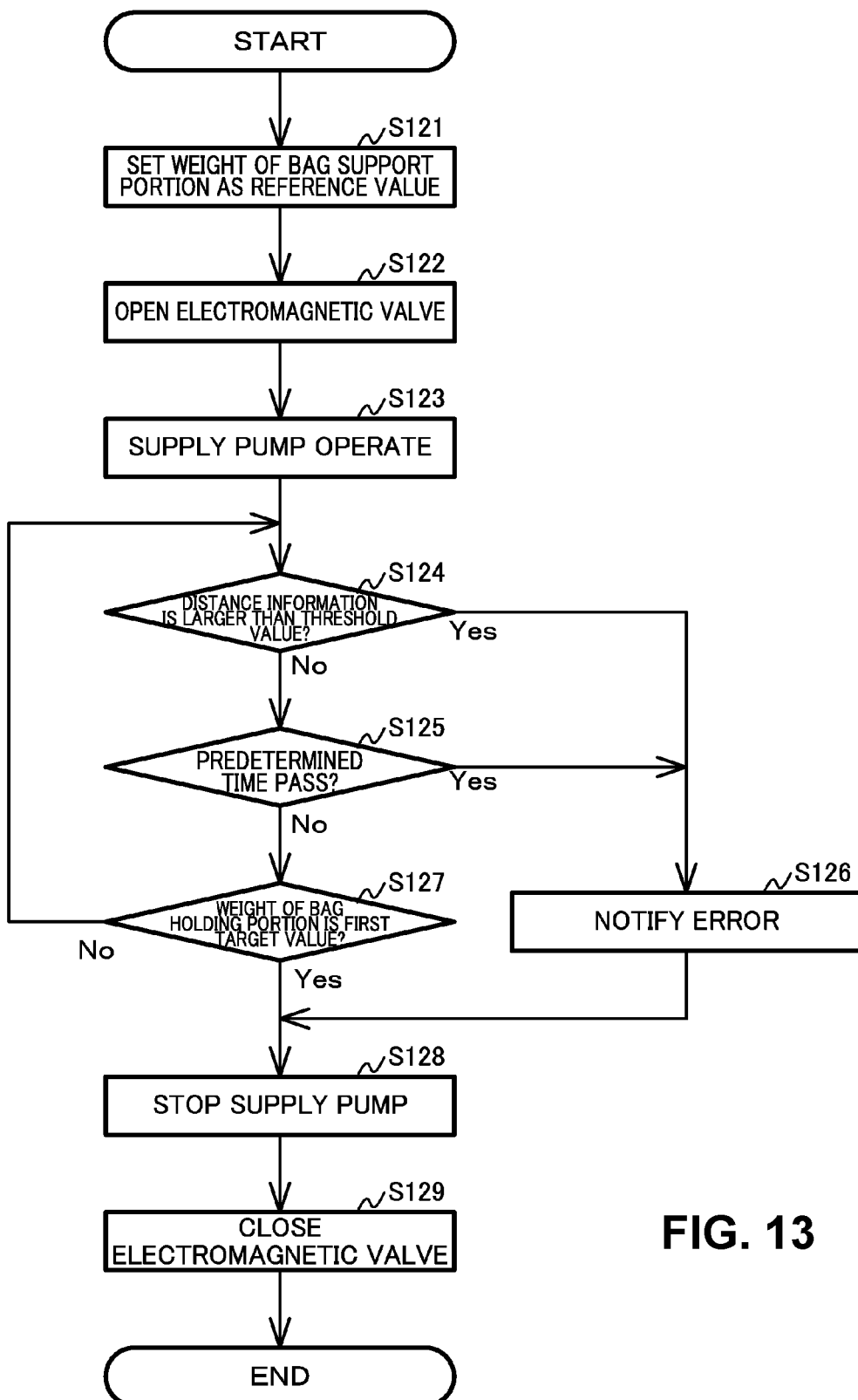
FIG. 13 is a flow chart of a liquid supply step.

Subsequently, the supply/discharge control portion 22 supplies a cell suspension to the culture bag 70 (Step S14). The supply of the cell suspension to the culture bag 70 is performed according to the liquid supply step. In detail, as illustrated in FIG. 13, when the first bag holding portion 31 stops at the first position, the weight detector 23 detects the weight of the culture bag 70 and the first bag holding portion 31. According to information on the weight output from the weight detector 23, the control portion 11 sets a first reference value (Step S121). Subsequently, the control portion 11 calculates a value obtained by adding the weight of a cell suspension to be supplied to the culture bag 70 to the first reference value as a first target value. The weight of a liquid to be supplied to the culture bag 70 can be calculated based on the capacity of a cell suspension to be supplied to the culture bag 70. Assuming that the specific gravity of various liquids, such as a cell suspension, a culture medium, and a peeling liquid, is approximately 1, it may be regarded that the capacity (mL) and the weight (g) are equal. In Step S14, the cell suspension is supplied to the culture bag 70 but Step S14 may be omitted and a cell suspension may be manually charged into the culture bag 70 beforehand.

When the first bag holding portion 31 is in the first position, the supply/discharge control portion 22 drives the liquid supply mechanism 81 to supply a liquid to the culture bag 70. In detail, the valves V6 and V9 are brought into the opened state (Step S122). Then, the supply pump 91 is driven (Step S123). The server bag 40 reserves beforehand a cell suspension containing cells to be cultured. Therefore, the cell suspension is supplied from the server bag 40 to the culture bag 70 through the port 73. While the cell suspension is being supplied to the culture bag 70, i.e., while the supply pump 91 is being driven, the control portion 11 monitors whether an output value of the distance sensor 67 exceeds a preset threshold value (Step 124). When the control portion 11 judges that an output value of the distance sensor 67 exceeds the threshold value (Step 124: Yes), the control portion 11 issues an alarm by generating a buzzer sound or turning on a light (Step S126). Then, the supply/discharge control portion 22 stops the supply pump 91 (Step S128).

The control portion 11 monitors whether preset time has passed after the supply pump 91 is driven (Step 125). As the time, time longer than time enough for the supply pump 91 to supply a maximum amount of liquid to the culture bag 70 is set. When the control portion 11 judges that the preset time has passed after the supply pump 91 is driven (Step 125: Yes), the control portion 11 issues an alarm in the same manner as above (Step S126), and then the supply/discharge control portion 22 stops the supply pump 91 (Step 128).

The control portion 11 monitors whether an output value of the weight detector 23 has reached the first target value while the supply pump 91 is being driven (Step 127). When the control portion 11 judges that the output value of the weight detector 23 has reached the first target value (Step 127: Yes), the supply/discharge control portion 22 stops the supply pump 91 (Step S128) to bring the valves V6 and V9 into the closed state (Step S129). Thus, the supply (liquid supply step) of the cell suspension to the culture bag 70 is completed (Step S14).

Figure 14:
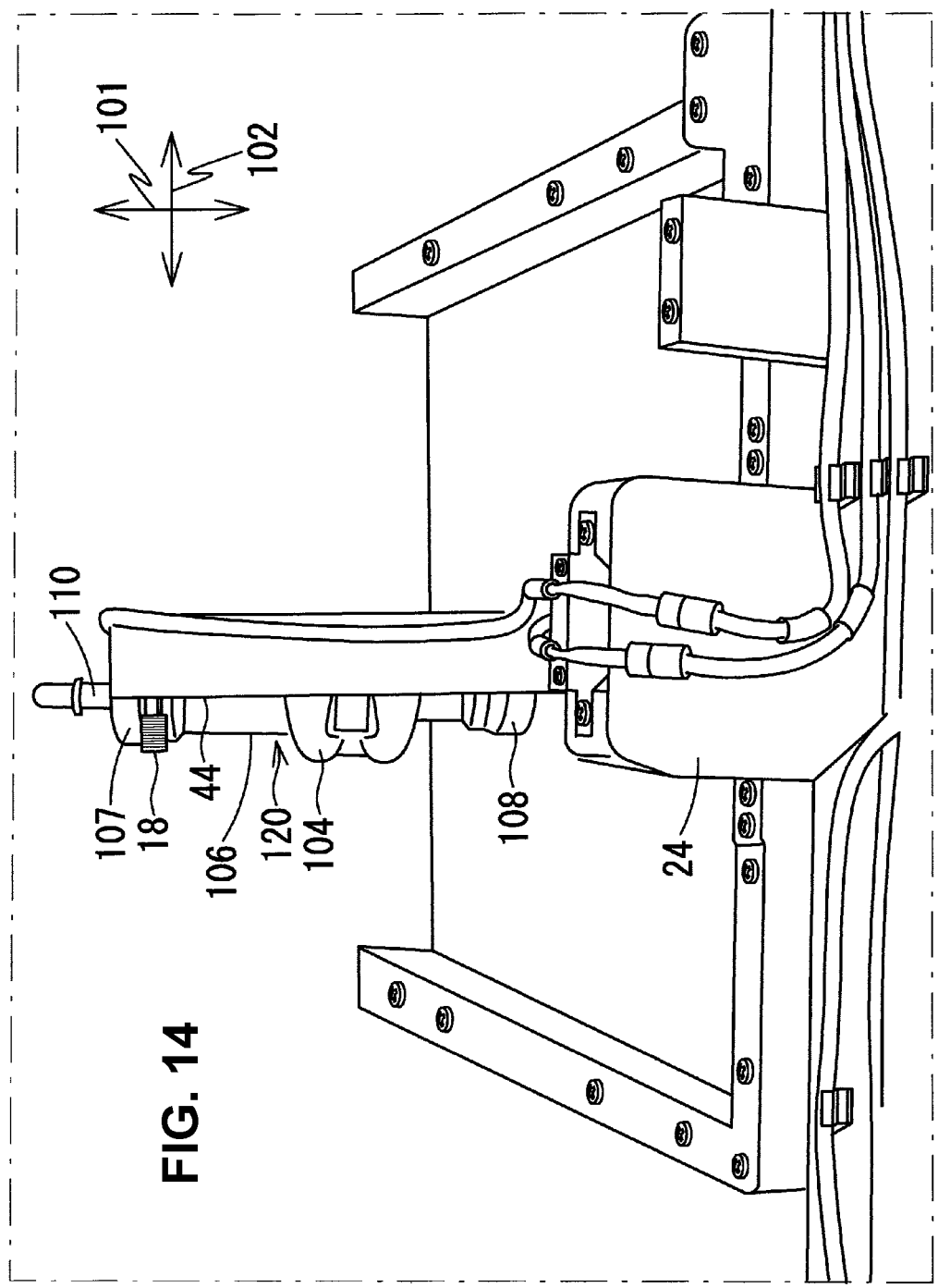
FIG. 14 is a schematic view for explaining a third position of the first bag holding portion 31.
Figure 15:
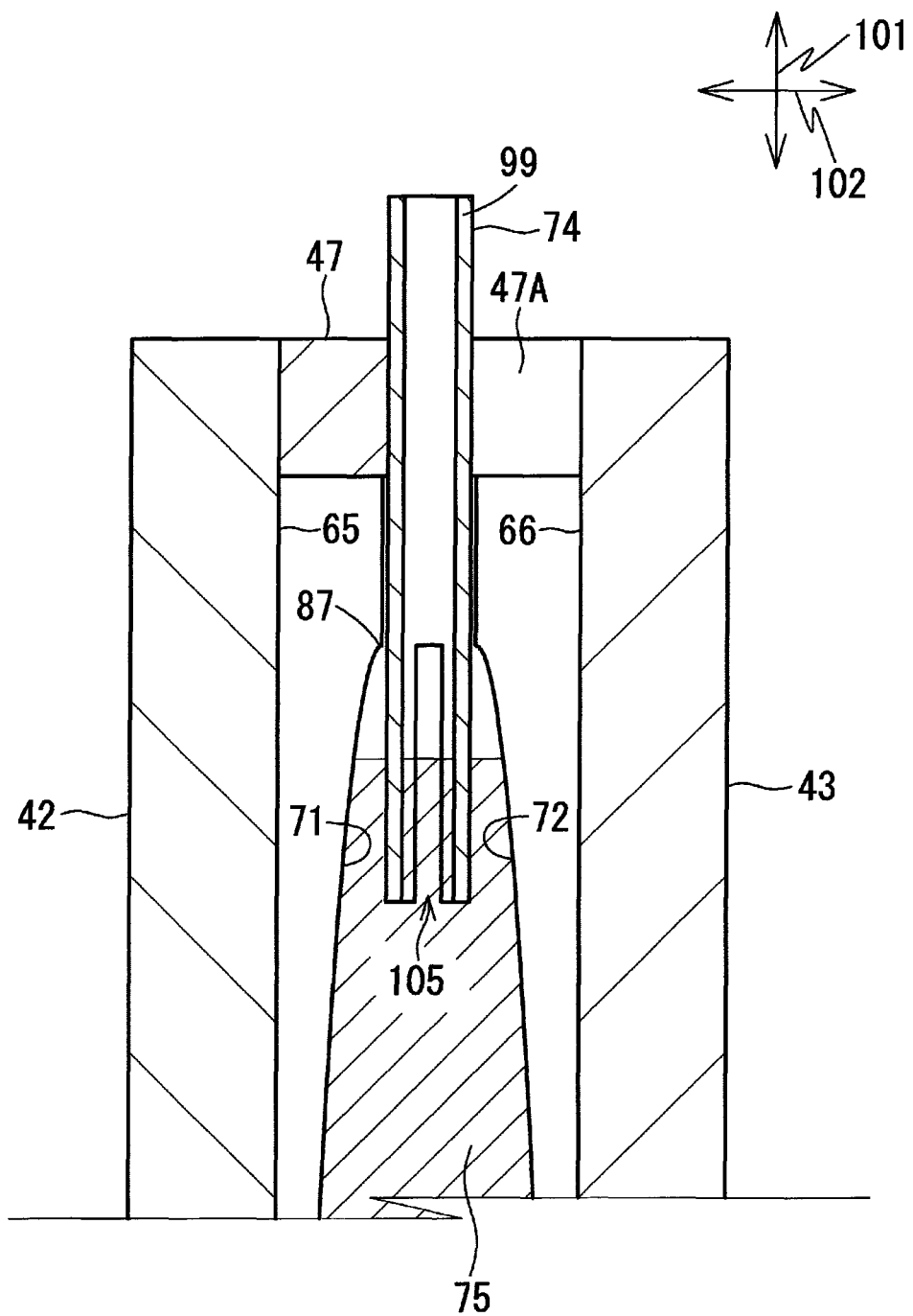
FIG. 15 is a cross-sectional view illustrating the cut plane V-V of the culture bag 70 when the first bag holding portion 31 is in the third position.

Subsequently, as illustrated in FIG. 11, the rotation control portion 20 drives the rotation mechanism 34 to rotate the first bag holding portion 31 counterclockwise by 90°. Thus, as illustrated in FIGS. 14 and 15, the first bag holding portion 31 is brought into a third position where the supporting surfaces 65 and 66 are in parallel with the vertical direction, the port 74 is located upward, and the port 73 is located downward (Step S15). To the edge 88 of the port 74 located upward in the culture bag 70 held by the first bag holding portion 31 in the third position, gas entering the internal space 75 gathers. Since the edge 88 has the tapered shape toward the port 74, the gas moving along the edge 88 gathers to the port 74. The supporting surfaces 65 and 66 in the third position may be in parallel with the approximately vertical direction and do not necessarily need to be strictly in parallel with the vertical direction.

The first bag holding portion 31 is brought into the third position, and then the supply/discharge control portion 22 brings the valves V6 and V9 into the closed state and brings the valves V13 and V15 into the opened state. Subsequently, the supply/discharge control portion 22 drives the discharge pump 92. Thus, a liquid or gas is discharged from the port 74 of the culture bag 70. When the gas remains in the internal space 75 of the culture bag 70 when a cell suspension is supplied to the culture bag 70, the gas is discharged from the internal space 75 through the port 74 (Step S16). Thus, a preliminary operation is completed.

After the preliminary operation is completed, the culture control portion 21 successively performs the culture step (Step S17), the culture medium exchanging step (Step S18), the culture step (Step S19), and the cell suspension collecting step (Step S20). The details of each step are described later. When a direction of performing subculture is input into the culture control portion 21 after the cell suspension collecting step (Step S21: Yes), a cell suspension collected by the other culture bags 80 and 90 is supplied in order to perform the subculture (Step S22). When a direction of performing subculture is not input (Step S22: No), the culture control portion 21 does not perform subculture. Thereafter, a cell suspension concentrating step (Step S23) is performed.

[Culture Step]

Figure 16:
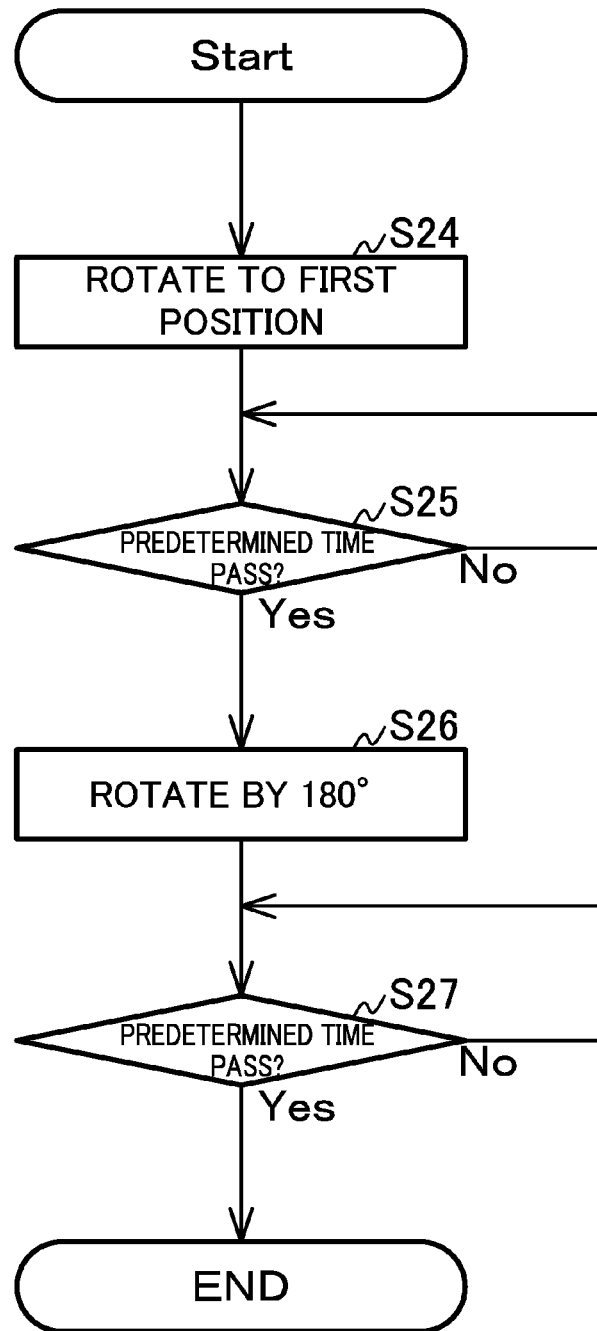
FIG. 16 is a flow chart of a culture step.
Figure 17A:
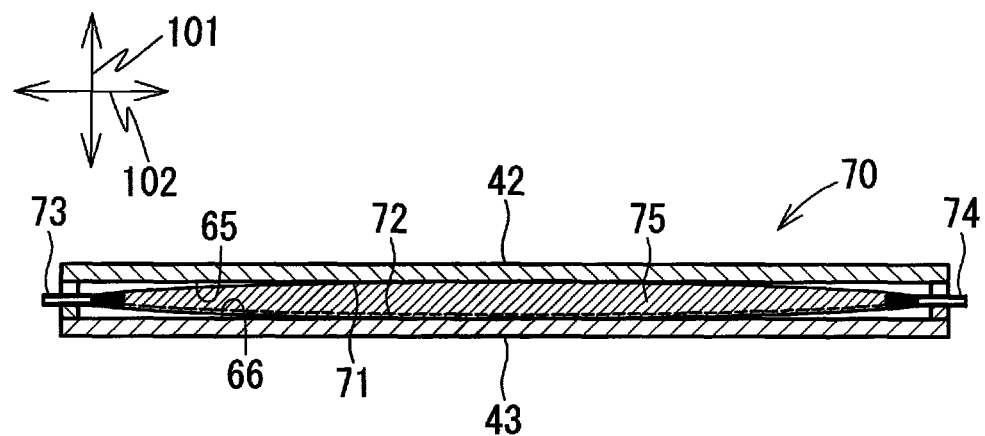
FIG. 17(A) is a cross-sectional view illustrating the cut plane V-V of the culture bag 70 when the first bag holding portion 31 is in the first position and FIG. 17(B) is a cross-sectional view illustrating the cut plane V-V of the culture bag 70 when the first bag holding portion 31 is in a fourth position.

Hereinafter, the culture step is described. When the culture step is performed, the culture control portion 21 outputs the first information to the rotation control portion 20 and the supply/discharge control portion 22. As illustrated in FIG. 12 and FIG. 16, the rotation control portion 20 drives the rotation mechanism 34 to bring the first bag holding portion 31 into the first position (Step S24). Thus, as illustrated in FIG. 17(A), the inner surface 71 is located upward and the inner surface 72 is located downward in the culture bag 70. The internal space 75 of the culture bag 70 reserves a cell suspension containing cells to be cultured and a culture medium. In the internal space 75, the cells descend in the cell suspension by gravity to contact the inner surface 72. Thus, the cells adhere to the inner surface 72 to be cultured.

Figure 17B:
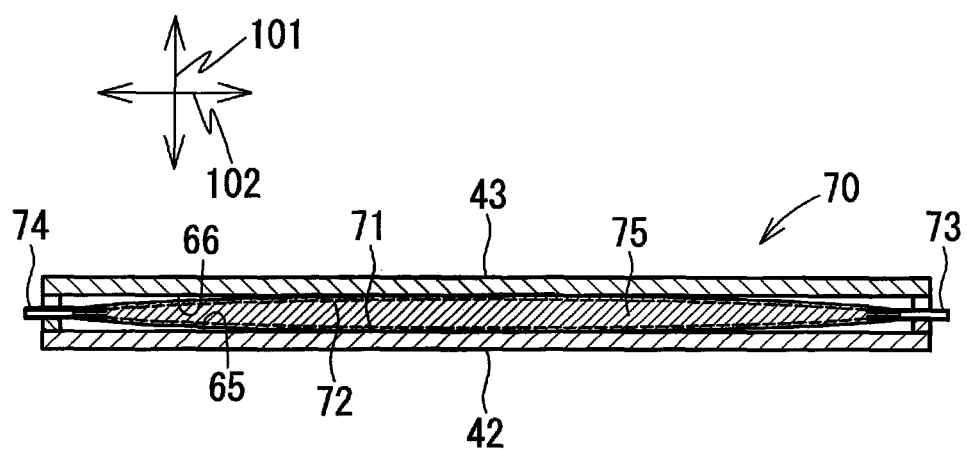

As illustrated in FIG. 16, the rotation control portion 20 maintains the first bag holding portion 31 in the first position until the preset time passes (Step S25: No). After the preset time has passed (Step S25: Yes), the rotation control portion 20 drives the rotation mechanism 34 to rotate the first bag holding portion 31 clockwise by 180° as viewed from the front of the concentrator 10 (Step S26). Thus, as illustrated in FIG. 17(B) and FIG. 18, the first bag holding portion 31 is brought into a fourth position in which the supporting surfaces 65 and 66 are in parallel with the horizontal direction, the inner surface 72 of the culture bag 70 is located upward, and the inner surface 71 is located downward. When the inner surface 72 is located upward and the inner surfaces 71 is located downward in the culture bag 70, cells contained in the cell suspension reserved in the internal space 75 of the culture bag 70 and not adhering to the inner surface 72 descend in the cell suspension by gravity to contact the inner surface 71. Thus, the cells adhere to the inner surface 71 to be cultured. The rotation control portion 20 maintains the first bag holding portion 31 in the fourth position until the preset time passes (Step S27: No). When the preset time has passed, the culture step is completed (Step S27: Yes).

[Culture Medium Exchanging Step]

Hereinafter, the culture medium exchanging step is described. When the culture medium exchanging step is performed, the culture control portion 21 outputs the second information to the rotation control portion 20 and the supply/discharge control portion 22. The valve V1 and the valve V7 through which the tubes 38, which are connected to the reservoir 117 reserving a fresh culture medium stored in the cold storage portion 12 or the normal temperature storage portion 13, are passed are brought into the opened state, and then the supply pump 91 is driven to supply the fresh culture medium to the server bag 39. Thereafter, the supply/discharge control portion 22 stops the supply pump 91, brings the valve V1 into the closed state, and then brings the valve V6 into the opened state. The supply/discharge control portion 22 brings the valves V6 and V7 through which the tubes 38, which are connected to the server bags 39 and 40, are passed into the opened state, and then reversely drives the supply pump 91 to supply a fresh culture medium to the server bag 40. Thereafter, the supply/discharge control portion 22 stops the supply pump 91, and then brings the valves V6 and V7 into the closed state. The fresh culture medium is held in the server bag 40 to be warmed to 37° C.

Figure 19:
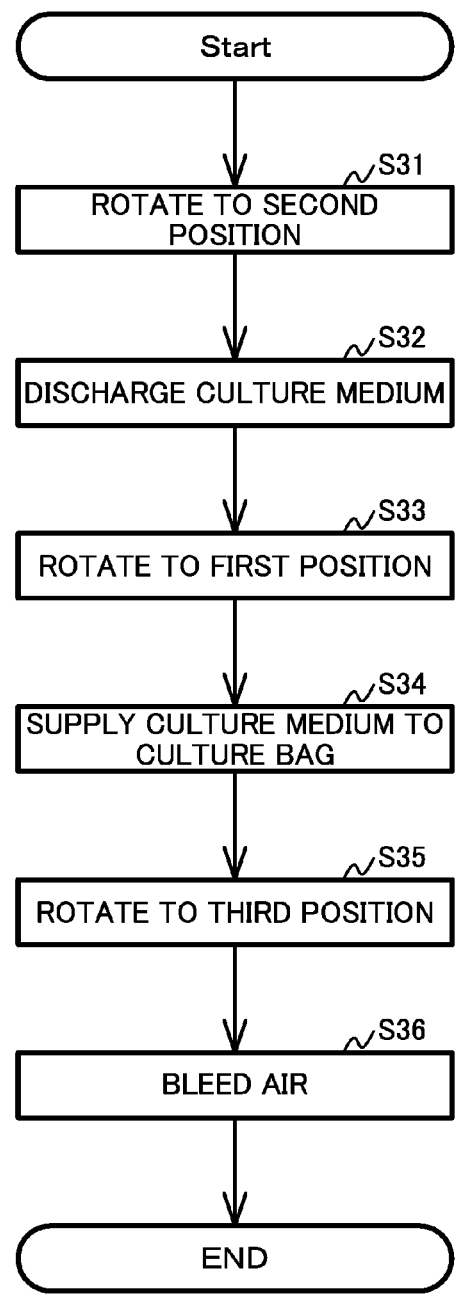
FIG. 19 is a flow chart of a culture medium exchanging step.
Figure 20:
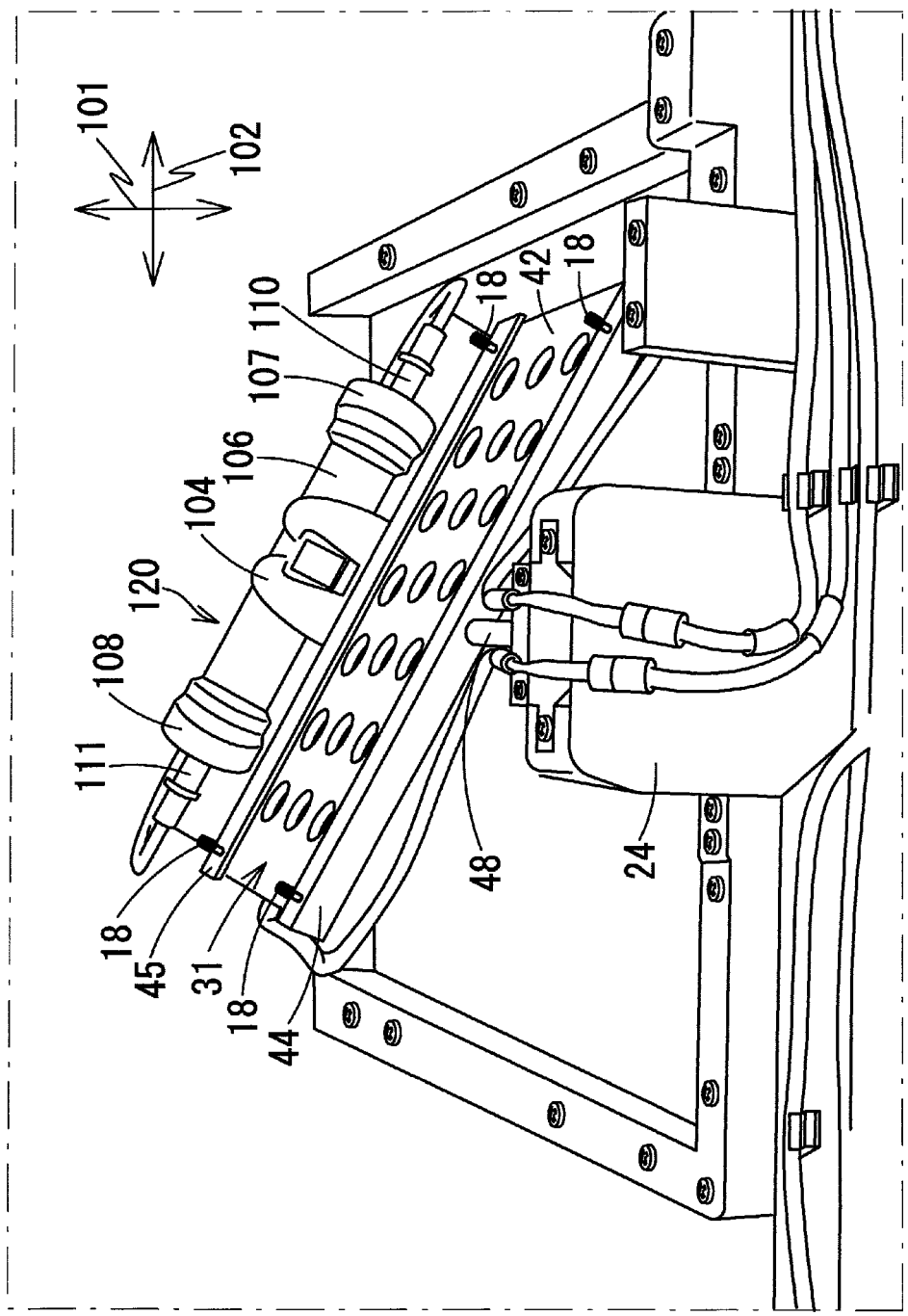
FIG. 20 is a schematic view for explaining a second position of the first bag holding portion 31.
Figure 21:
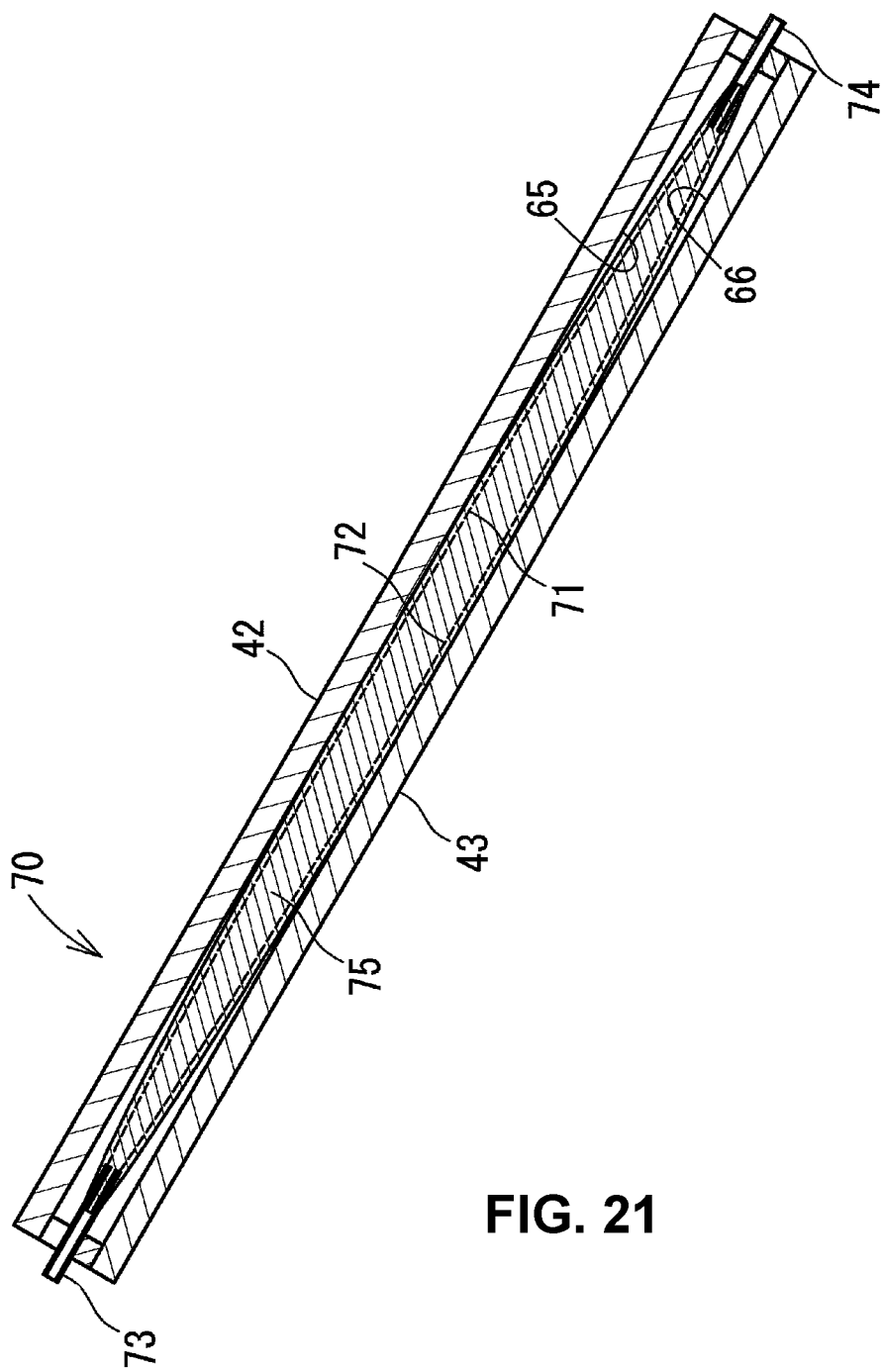
FIG. 21 is a cross-sectional view illustrating the cut plane V-V of the culture bag 70 when the first bag holding portion 31 is in the second position.

As illustrated in FIG. 19, the rotation control portion 20 drives the rotation mechanism 34 to rotate the first bag holding portion 31 in the first position clockwise by 30° as viewed from the front of the concentrator 10. Thus, as illustrated in FIGS. 20 and 21, the first bag holding portion 31 is brought into the second position in which the acute angle formed by the supporting surfaces 65 and 66 with respect to the horizontal direction is 30° and the port 73 is located upward and the port 74 is located downward (Step S31). In the second position, the acute angle formed by the supporting surfaces 65 and 66 with respect to the horizontal direction is not limited to 30° and may be arbitrarily set insofar as the supporting surfaces 65 and 66 are not in parallel with the horizontal direction and the vertical direction. Preferably, the acute angle formed by the supporting surfaces 65 and 66 with respect to the horizontal direction is 20° or more and 70° or less. More preferably, the acute angle is 30° or more and 60° or less.

Figure 22:
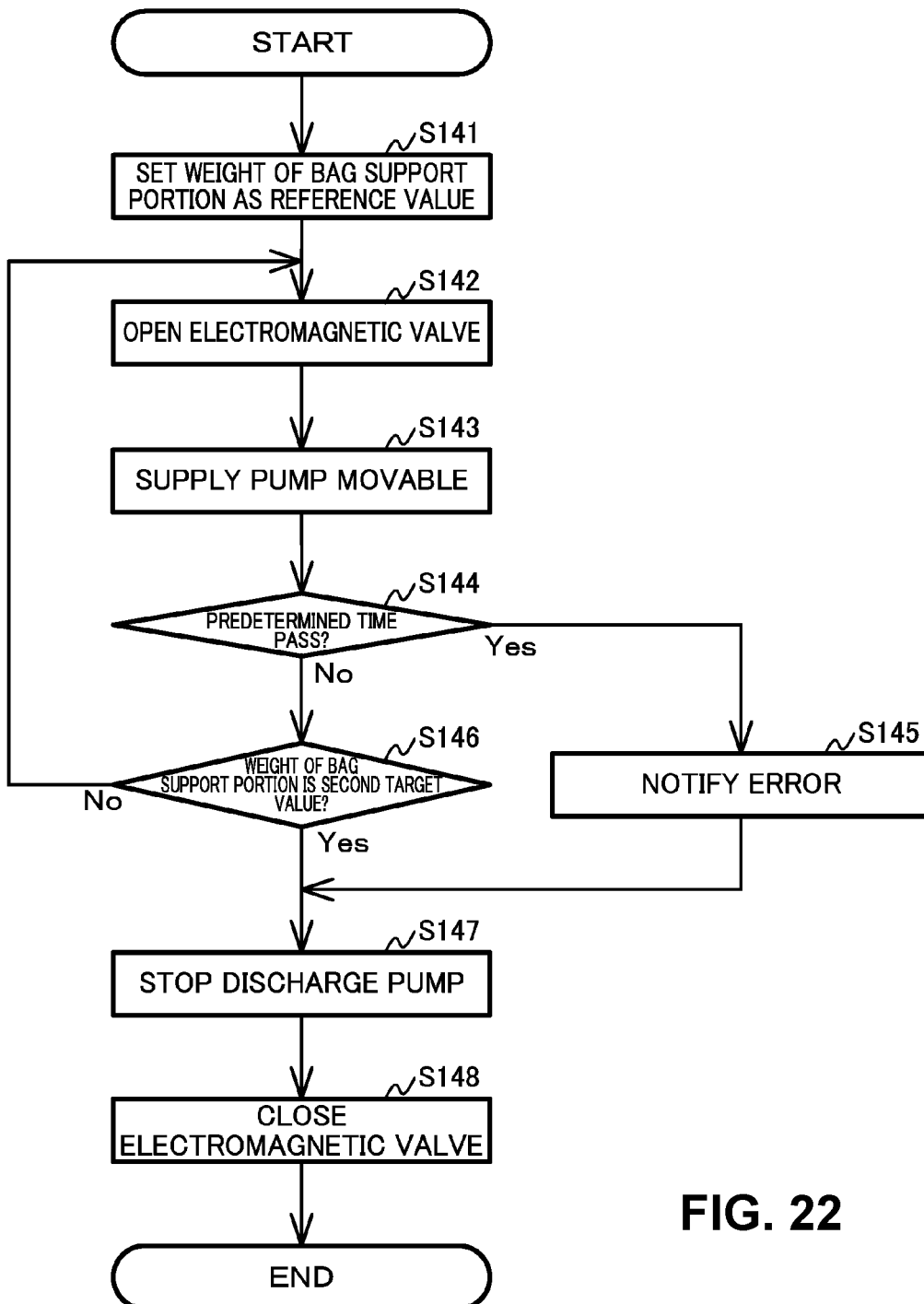
FIG. 22 is a flow chart of a liquid discharging step.

Subsequently, the supply/discharge control portion 22 discharges the culture medium from the culture bag 70 (Step S32). The discharge of the culture medium from the culture bag 70 is performed according to the liquid supply step. In detail, when the first bag holding portion 31 stops at the second position as illustrated in FIG. 22, the weight detector 23 detects the weights of the culture bag 70 and the first bag holding portion 31. According to information on the weight output from the weight detector 23, the control portion 11 sets a second reference value (Step S141). Subsequently, the control portion 11 calculates a value obtained by subtracting the weight of a culture medium to be discharged from the culture bag 70 from the second reference value as a second target value.

When the first bag holding portion 31 stops at the second position, the supply/discharge control portion 22 drives the liquid discharge mechanism 82 to discharge the culture medium from the culture bag 70. When described in detail, the valves V13 and V15 are brought into the opened state (Step S142). Subsequently, the discharge pump 92 is driven (Step S143). The control portion 11 monitors whether the preset time has passed after the discharge pump 92 is driven (Step S144). As the time, time longer than time enough for the discharge pump 92 to discharge the half amount of a liquid from the culture bag 70 is set. When the control portion 11 judges that the preset time has passed after the discharge pump 92 is driven (Step 144: Yes), the control portion 11 issues an alarm in the same manner as above (Step S145), and then the supply/discharge control portion 22 stops the discharge pump 92 (Step 147).

The control portion 11 monitors whether the output value of the weight detector 23 has reached the second target value while the discharge pump 92 is being driven (Step 146). When the control portion 11 judges that the output value of the weight detector 23 has reached the second target value (Step 146: Yes), the supply/discharge control portion 22 stops the discharge pump 92 (Step S147) and brings the valves V13 and V15 into the closed state (Step S148). Thus, the half of the culture medium reserved in the culture bag 70 is discharged from the internal space 75 of the culture bag 70 (Liquid discharging step) (Step S32). Due to the fact that the first bag holding portion 31 is maintained at the second position, the discharge of the culture medium from the port 74 is facilitated. Even when the half of the culture medium is discharged from the culture bag 70, the inner surfaces 71 and 72 of the culture bag 70 are difficult to contact each other as illustrated in FIG. 21.

As illustrated in FIG. 19, after the half culture medium is discharged from the culture bag 70, the rotation control portion 20 drives the rotation mechanisms 34 to bring the first bag holding portion 31 into the first position (Step S33). After the first bag holding portion 31 is brought into the first position, the valve V6 and V9 are brought into the opened state, and then the supply of the culture medium to the culture bag 70 is performed in the same manner as in the liquid supply step described above. Thus, the fresh culture medium reserved in the server bag 40 is supplied to the culture bag 70 (Step S34). The amount of the fresh culture medium to be supplied to the culture bag 70 is the same as the amount of the culture medium previously discharged from the culture bag 70, i.e., the half amount of the culture medium reserved in the internal space 75. After the fresh culture medium is supplied to the culture bag 70, the supply/discharge control portion 22 stops the supply pump 91, and then brings the valve V6 and V9 into the closed state.

After the fresh culture medium is supplied to the culture bag 70, the rotation control portion 20 drives the rotation mechanism 34 to rotate the first bag holding portion 31 in the first position counterclockwise by 90° as viewed from the front of the concentrator 10. Thus, as illustrated in FIG. 14, the first bag holding portion 31 is brought into the third position in which the supporting surfaces 65 and 66 are in parallel with the vertical direction, the port 73 is located downward, and the port 74 is located upward (Step S35). After the first bag holding portion 31 is brought into the third position, the supply/discharge control portion 22 brings the valves V13 and V15 into the opened state, and then drives the discharge pump 92. Thus, even when gas is mixed in the internal space 75 of the culture bag 70, the gas is discharged from the internal space 75 with the culture medium through the port 74 (Step S36). Then, the discharge pump 92 is stopped, and then the valves V13 and V15 are brought into the closed state, so that the culture medium exchanging step (Step S18) is completed.

When the culture medium exchanging step (Step S18) is completed, the culture step (Step S19) is performed in the same manner as above. The culture medium exchanging step and the culture step may be further repeated after subculture. When the amount of the cells increases in the culture step repeated after subculture, the cell suspension may be moved to the culture bags 80 and 90 from the culture bag 70 so that the culture bags 80 and 90 having a capacity larger than that of the culture bag 70 are used. After the culture step (Step S19) repeatedly performed as necessary, the cell suspension collecting step (Step S20) and the cell suspension concentrating step (Step S23) are performed.

[Cell Suspension Collecting Step]

Hereinafter, the cell suspension collecting step is described. When the cell suspension collecting step is performed, the culture control portion 21 outputs the third information to the rotation control portion 20 and the supply/discharge control portion 22.

Figure 23:
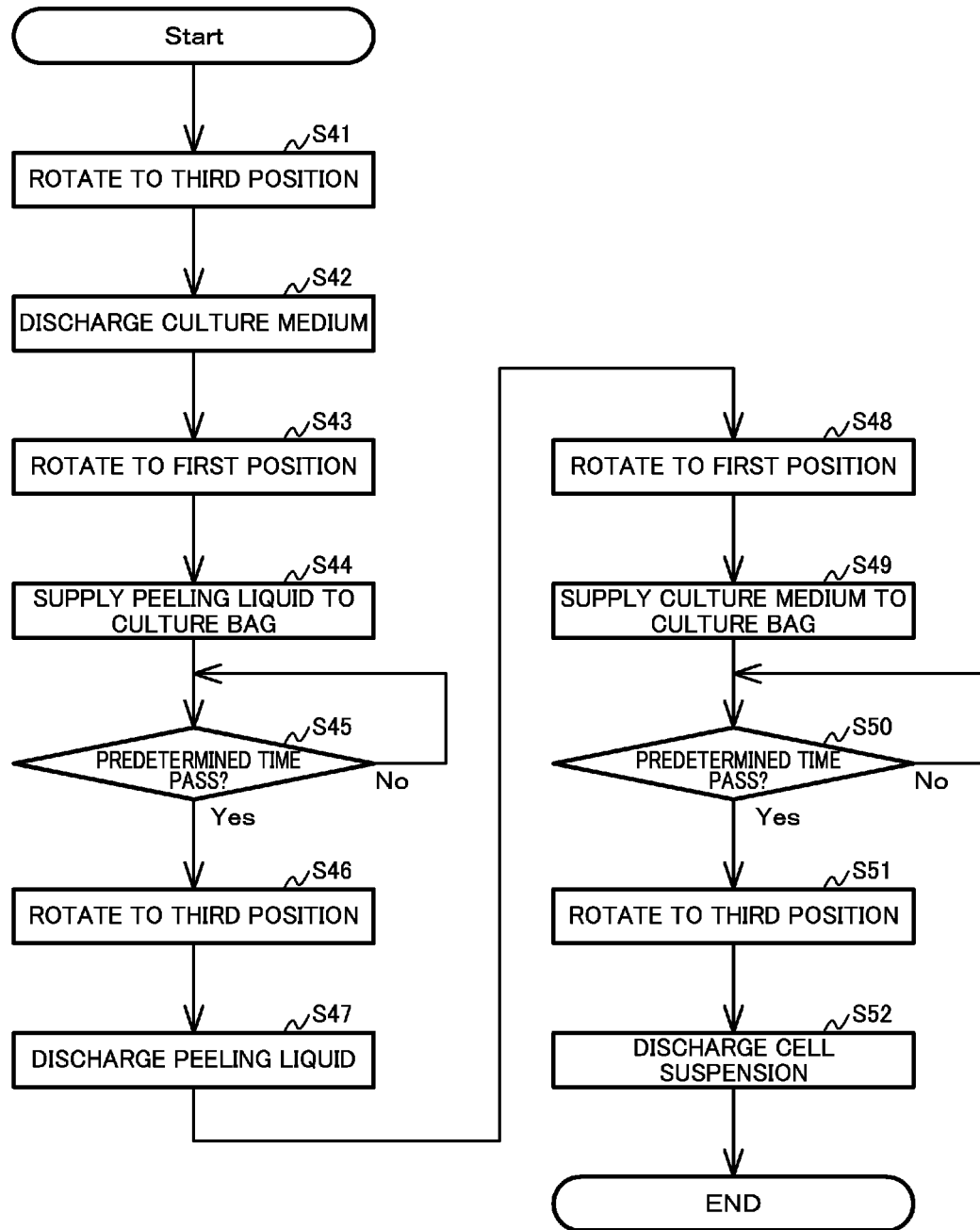
FIG. 23 is a flow chart of a cell suspension collecting step.
Figure 24:
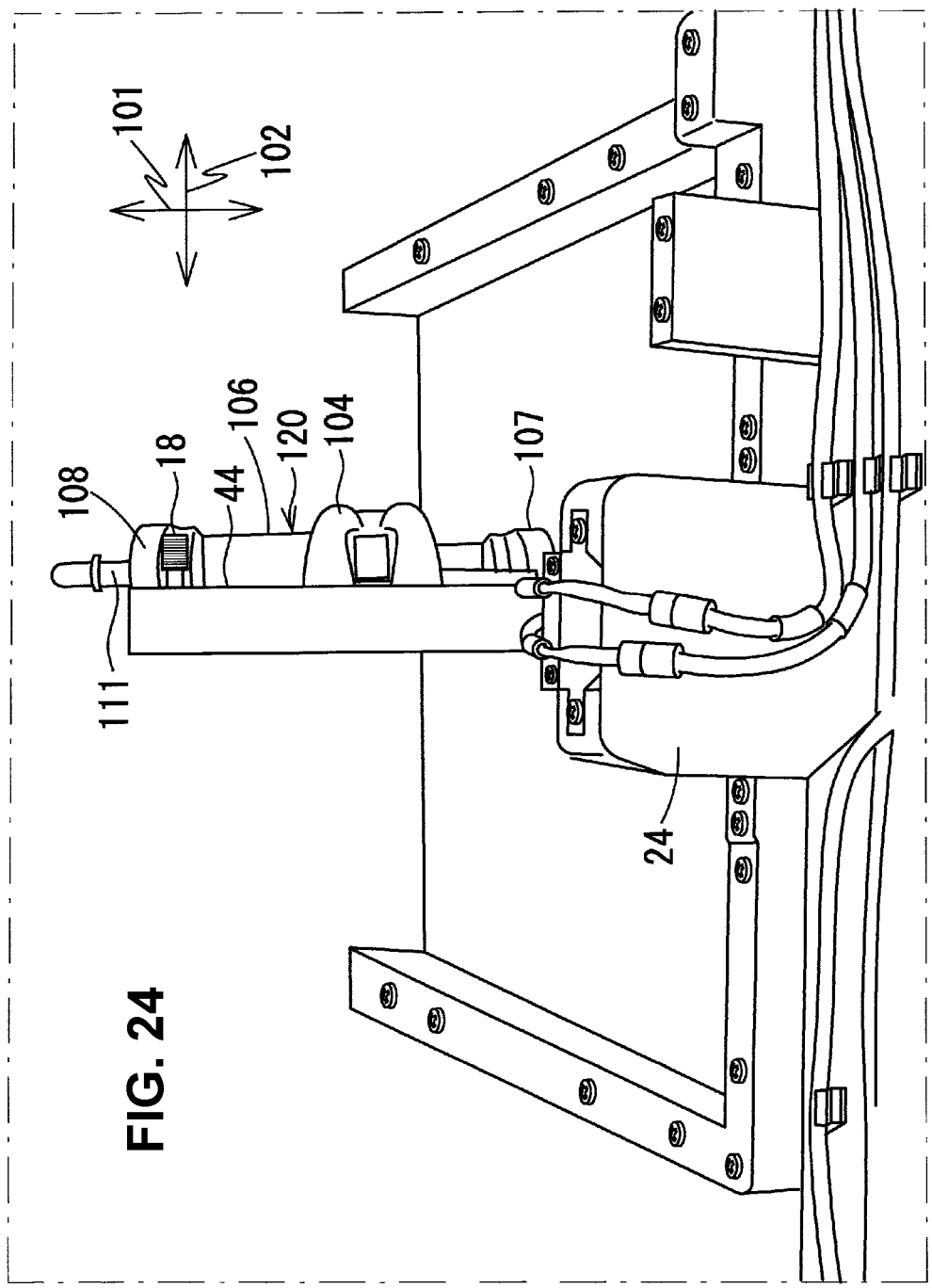
FIG. 24 is a schematic view for explaining the first bag holding portion 31 in a reverse third position.
Figure 25:
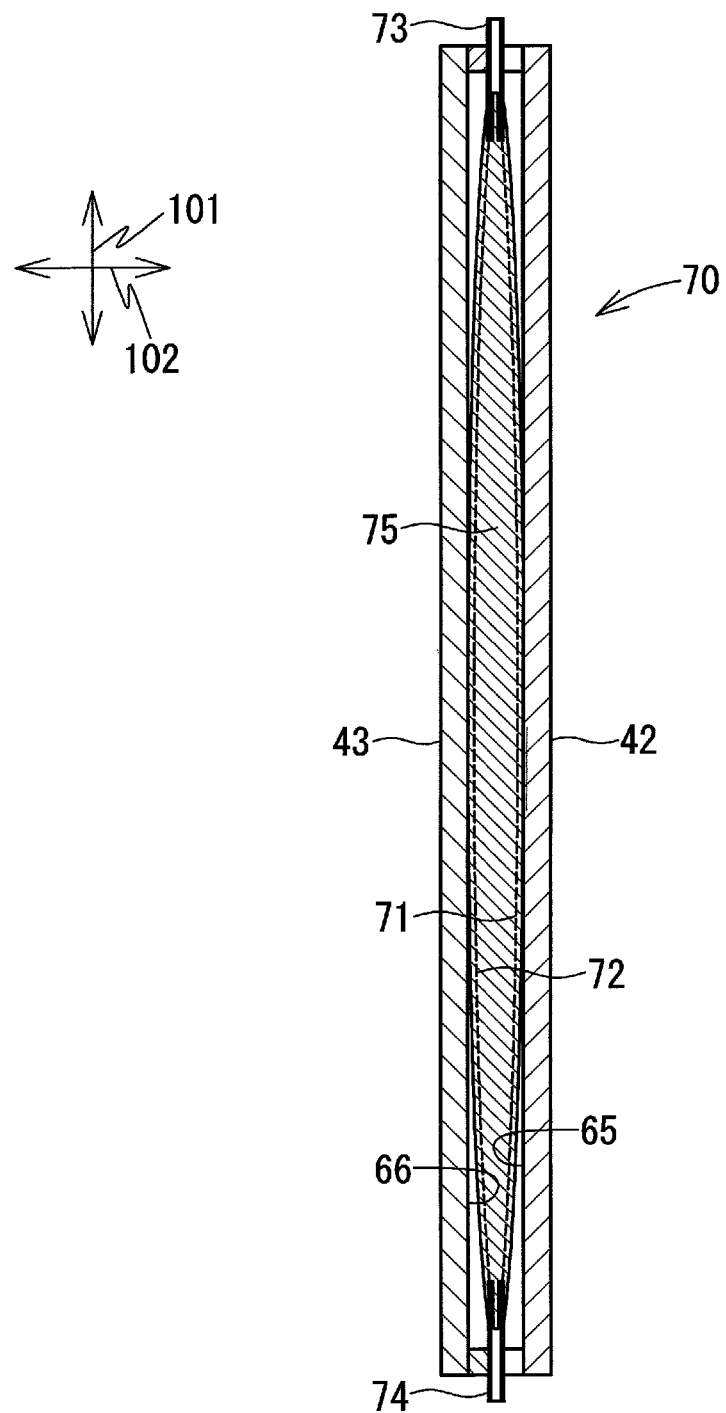
FIG. 25 is a cross-sectional view illustrating the cut plane V-V of the culture bag 70 when the first bag holding portion 31 is in the reverse third position.

As illustrated in FIG. 23, the rotation control portion 20 drives the rotation mechanism 34 to rotate the first bag holding portion 31 in the fourth position counterclockwise by 90° as viewed from the front of the concentrator 10. Thus, as illustrated in FIG. 24 and FIG. 25, the first bag holding portion 31 is brought into the third position in which the supporting surfaces 65 and 66 are in parallel with the vertical direction, the port 73 is located upward, and the port 74 is located downward (Step S41). In this embodiment, any position is referred to as the third position insofar as the supporting surfaces 65 and 66 of the first bag holding portion 31 are in parallel with the vertical direction irrespective of the positions (upward or downward) of the ports 73 and 74.

As illustrated in FIG. 23, after the first bag holding portion 31 is brought into the third position, the culture medium is discharged from the culture bag 70. The supply/discharge control portion 22 brings the valve V13 and V15 into the opened state, and then drives the discharge pump 92. Thus, the entire amount of the culture medium reserved in the culture bag 70 is discharged from the internal space 75 through the port 74 (Step S42). After the entire amount of the culture medium is discharged from the culture bag 70, the rotation control portion 20 drives the rotation mechanism 34 to bring the first bag holding portion 31 in the third position into the first position (Step S43).

After the first bag holding portion 31 is brought into the first position, a peeling liquid is supplied to the culture bag 70. The supply/discharge control portion 22 brings any one of the valves V3 to V5 through which the tube 38, which is connected to a vessel reserving a peeling liquid stored in the cold storage portion 12 or the normal temperature storage portion 13, is passed and the valve V9 into the opened state, and then drives the supply pump 91. Thus, the peeling liquid is supplied to the internal space 75 of the culture bag 70 through the port 73 (Step S44). After the peeling liquid is supplied to the culture bag 70, the supply/discharge control portion 22 stops the supply pump 91, and then brings any one of the valves V3 to V5 and V9, which are brought into the opened state, into the closed state. The rotation control portion 20 maintains the first bag holding portion 31 in the first position until the preset time passes (Step S45: No). The peeling liquid weakens the adhesion to the inner surfaces 71 and 72 of the culture bag 70 of the cells adhering to the inner surfaces 71 and 72. Such an action of weakening the adhesion of the cells to the inner surfaces 71 and 72 is realized by setting the type and the concentration of the peeling liquid, the contact time with the inner surfaces 71 and 72, the position of, for example, the first bag holding portion 31, and the like as appropriate. After the peeling liquid is supplied to the culture bag 70, gas may be discharged from the internal space 75 of the culture bag 70 as necessary in the same manner as above.

After the preset time has passed (Step S45: Yes), the rotation control portion 20 drives the rotation mechanism 34 to rotate the first bag holding portion 31 counterclockwise by 90° as viewed from the front of the concentrator 10 to bring the same into the third position (Step S46). After the first bag holding portion 31 is brought into the third position, the discharge of the cell suspension from the culture bag 70 is performed in the same manner as in the liquid discharging step described above. The supply/discharge control portion 22 brings the valves V6 and V9 into the opened state, and then reversely drives the supply pump 91. Thus, the peeling liquid is discharged from the internal space 75 through the port 73 in the culture bag 70 to the waste liquid vessel 19 (Step S47). After the entire amount of the peeling liquid is discharged from the culture bag 70, the rotation control portion 20 drives the rotation mechanism 34 to rotate the first bag holding portion 31 clockwise by 90° as viewed from the front of the concentrator 10 to bring the same into the first position (Step S48).

After the first bag holding portion 31 is brought into the first position, a culture medium is supplied to the culture bag 70. The supply/discharge control portion 22 brings any one of the valves V3 to V5 through which the tube 38, which is connected to a vessel reserving the culture medium stored in the cold storage portion 12 or the normal temperature storage portion 13, is passed and the valve V9 into the opened state, and then drives the supply pump 91. Thus, the culture medium is supplied to the internal space 75 of the culture bag 70 through the port 73 (Step S49). After the culture medium is supplied to the culture bag 70, the supply/discharge control portion 22 stops the supply pump 91, and then brings any one of the valves V3 to V5 and V9, which are brought into the opened state, into the closed state. The rotation control portion 20 maintains the first bag holding portion 31 in the first position until the preset time passes (Step S50). By the supply of the culture medium, the cells adhering to the inner surfaces 71 and 72 of the culture bag 70 are peeled off. The peeling of the cells from the inner surfaces 71 and 72 by the supply of the culture medium is realized by setting the flow velocity of the culture medium, the position of, for example, the first bag holding portion 31, the period of time when it is allowed to stand, and the like as appropriate. After the culture medium is supplied to the culture bag 70, gas may be discharged from the internal space 75 of the culture bag 70 as necessary in the same manner as above.

After the preset time has passed (Step S50), the rotation control portion 20 drives the rotation mechanism 34 to rotate the first bag holding portion 31 counterclockwise by 90° as viewed from the front of the concentrator 10 to bring the same into the third position (Step S51). After the first bag holding portion 31 is brought into the third position, the discharge of a cell suspension from the culture bag 70 is performed in the same manner as in the liquid discharging step described above. The supply/discharge control portion 22 brings the valves V6 and V9 into the opened state, and then reversely drives the supply pump 91. Thus, the cell suspension is discharged from the internal space 75 through the port 73 (Step S52) in the culture bag 70 to be collected by the server bag 40. Thus, the cell suspension collecting step (Step S20) is completed.

[Cell Suspension Concentrating Step]

Hereinafter, the cell suspension concentrating step (Step S23) is described. A method for concentrating a cell suspension using the filtering device 120 includes each step described below.

(4-1) Moving step of moving a cell suspension to the server bag 40 from the culture bag 70.
(4-2) Priming step of supplying a priming liquid to the filtering device 120.
(4-3) Filtering step of supplying a cell suspension to the filtering device 120.
(4-4) Collecting step of collecting a cell suspension from the filtering device 120.

Figure 26:
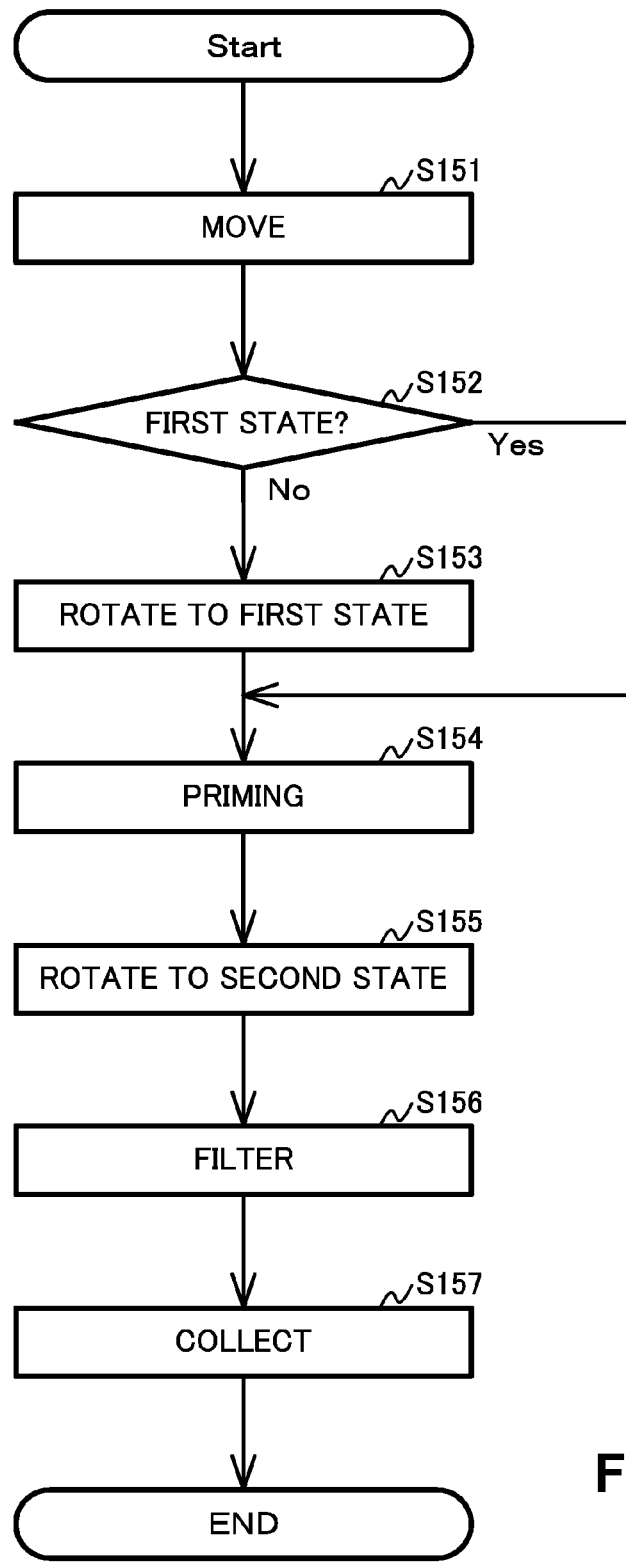
FIG. 26 is a flow chart of a cell suspension concentrating step.

As illustrated in FIG. 26, a cell suspension is moved to the server bag 40 from the culture bag 70 (Step S151). The moving step is performed in the cell suspension collecting step described above.

Subsequently, the rotation control portion 20 judges whether the filtering device support portion 104 is in a first state (Step S152). The first state is a state where the axial direction of the body 106 of the filtering device 120 is in parallel with the vertical direction and the inflow port 110 is located downward relative to the first discharge port 111 (FIG. 7(B)). When the filtering device support portion 104 is not in the first state (Step S152: No), the rotation control portion 20 drives the rotation mechanism 34 to rotate the filtering device support portion 104 to the first position (Step S153). In the first state, the axial direction of the body 106 of the filtering device 120 does not necessarily need to be in parallel with the vertical direction.

Then, priming (Step S154) is performed. As illustrated in FIG. 7(B), a priming liquid is supplied to the filtering device 120 supported by the filtering device support portion 104 in the first state. The priming liquid is a phosphate buffer or the like, for example. The supply/discharge control portion 22 brings the valve V2 connected to the reservoir 116 which is held by the cold storage portion 12 or the normal temperature storage portion 13 and reserves the priming liquid and the valve V8, V13, and V14 into the opened state, and then drives the supply pump 91. Thus, the priming liquid is supplied to the filtering device 120 through the inflow port 110. The air, substances charged for storing the hollow fiber bundle 109, and the like are discharged from the first outflow port 111 of the filtering device 120 in such a manner as to be pressed out by the priming liquid. The supply/discharge control portion 22 monitors whether the preset time has passed after the supply pump 91 is driven. As the time, time longer than time enough for the supply pump 91 to discharge the gas from the inside of the filtering device 120 is set. When the supply/discharge control portion 22 judges that the preset time has passed after the supply pump 91 is driven, the supply/discharge control portion 22 stops the supply pump 91, and then brings the valve V2 and the valves V13 and V14 into the closed state. Thus, the priming step is completed.

After the priming step is completed, the rotation control portion 20 drives the rotation mechanisms 34 to rotate the filtering device support portion 104 by 180° (Step S155). Thus, as illustrated in FIG. 7(C), the filtering device 120 is brought into a second state. The second state is a state where the axial direction of the body 106 of the filtering device 120 is in parallel with the vertical direction and the inflow port 110 is located upward relative to the first discharge port 111. In the second state, the axial direction of the body 106 of the filtering device 120 does not necessarily need to be in parallel with the vertical direction.

Subsequently, the filtering step (Step S156) is performed. The supply/discharge control portion 22 brings the valves V6 and V12 into the opened state, and then drives the supply pump 91. Thus, a cell suspension is supplied to the filtering device 120 through the inflow port 110 from the server bag 40. The cell suspension supplied to the filtering device 120 flows through the inside of the hollow fiber bundle 109, and then cells contained in the cell suspension precipitate to the downside of the inside of the hollow fiber bundle 109 by gravity to stay near the first outflow port 111. On the other hand, a liquid, such as a culture medium, contained in the cell suspension flows out to the outside of the hollow fiber bundle 109 while flowing downward in the internal space of the hollow fiber bundle 109, and then is caused to flow out to the outside of the filtering device 120 through the second outflow port 112. Thus, the cell suspension which is caused to flow in the filtering device 120 is held in a concentrated state in the hollow fiber bundle 109 and near the first outflow port 111 located downward in the gravity direction. After the entire amount of the cell suspension is supplied to the filtering device 120, the supply/discharge control portion 22 stops the supply pump 91, and then brings the valve V6 and V12 into the closed state. Thus, the filtering step is completed (Step S156).

Subsequently, the collecting step (Step S157) is performed. The supply/discharge control portion 22 brings the valve V1 connected to the reservoir 117 reserving the fresh culture medium stored in the cold storage portion 12 or the normal temperature storage portion 13 and the valves V14 and V18 into the opened state, and then drives the supply pump 91. Thus, the fresh culture medium is supplied to the filtering device 120 through the inflow port 110 as illustrated in FIG. 7(D). In the filtering device 120, the fresh culture medium flowing through the hollow fiber bundle 109 is caused to flow out of the filtering device 120 to the collection bag 41 through the first discharge port 111 with the concentrated cell suspension. Thus, the collecting step is completed (Step S157). The concentrated cell suspension is caused to flow in the collection bag 41 but may be caused to flow in the culture bags 70, 80, and 90.

Operational Effects of this Embodiment

According to this embodiment, the inflow and the outflow of a liquid in/from the culture bag 70 or the filtering device 120 are separated into the liquid supply circuit and the liquid discharge circuit, which reduces a possibility that the liquid which is caused to flow out of the culture bag 70 or the filtering device 120 is mixed with the liquid which is caused to flow in the culture bag 70 or the filtering device 120. On the other hand, in the priming of the filtering device 120, a priming liquid is caused to flow in from the inflow port 110 located downward in the filtering device 120 and gas or the like is discharged from the outflow port 110 located upward in the filtering device 120. In the concentration of the cell suspension, the cell suspension is caused to flow in from the inflow port 110 located above the filtering device 120, and then the cell suspension is concentrated by the hollow fiber bundle 109. Then, the concentrated cell suspension is caused to flow out of the first outflow port 110 located downward in the filtering device 120. Thus, the cell suspension containing the cells cultured in the culture bag 70 can be simply and efficiently concentrated.

Moreover, the positions in the vertical direction of the ports 73 and 74 of the culture bag 70 change by the rotation of the first bag holding portion 31 and the like, and therefore the culture bag 70 can be brought into a position suitable for culturing, culture-medium exchange, collection of a cell suspension, and the like.

Moreover, the rotation mechanism 34 integrally rotates the first bag holding portion 31 and the filtering device support part 104, and therefore the size of the concentrator 10 is reduced.

Modification

Although the embodiment described above describes the culture bags 70, 80, and 90 as the culture vessel, the culture vessel is not limited to a bag-shaped substance and substances having shapes with flexibility, such as a bottle and a cassette, may be used. Similarly, the server bags 39 and 40 and the like are not limited to a bag-shaped substance and substances having shapes with flexibility, such as a bottle and a cassette, may be used.

Moreover, the embodiment described above describes the configuration in which the rotation mechanism 34 integrally rotates the first bag holding portion 31 and the filtering device support portion 104 but a configuration may be acceptable in which the first bag holding portion 31 and the filtering device support portion 104 are individually and independently rotated by a separate rotation mechanism (for example, a rotation mechanism and a second rotation mechanism).

Moreover, the embodiment described above describes one having the hollow fiber bunch 109 as the filtering device 120 but a filtering device having a filtration membrane (dialysis membrane) other than hollow fiber bunch 109 may be used.

Moreover, the configuration of the culture circuit described in the embodiment described above is merely one example. It is a matter of course that the configuration of the culture circuit may be altered insofar as the scope of the present invention is not altered, e.g., the server bags 39 and 40 and the like are omitted and another vessel and the like are added as appropriate. Moreover, pumps other than the tube pump may be used as the supply pump 91 and the discharge pump 92. Moreover, those other than the valve may be used as the switching mechanism of the flow passages of the culture circuit.

The embodiment described above describes the example of culturing adhesive cells but cells other than the adhesive cells may be cultured by the culture device 10.

REFERENCE SIGNS LIST

10 Concentrator
11 Control portion
22 Supply/discharge control portion
31, 32, 33 Bag holding portion
34 Rotation mechanism
37 Liquid supply/discharge mechanism
38 Tube
40 Server bag
41 Collection bag
48, 49 Rotation shaft
70, 80, 90 Culture bag
73, 74 Port
91 Supply pump
92 Discharge pump
95 to 98 Port
106 Body
109 Hollow fiber bundle
110 Inflow port
111 First outflow port
112 Second outflow port
116, 117 Reservoir
120 Filtering device
V1 to V18 Valve

The invention claimed is:

1. A concentrator comprising:
a filtering device having a case provided with a filtration membrane in an internal space, an inflow port and a first outflow port bringing an inside of the filtration membrane and an outside of the case into communication with each other, and a second outflow port bringing an outside of the filtration membrane and an outside into communication with each other;
a liquid supply circuit connected to the inflow port;
a liquid discharge circuit connected to the first outflow port and the second outflow port;
a shaft that is rotatable and to which the filtering device is mechanically linked to rotate with the shaft so that positions in a vertical direction of the inflow port and the first outflow port change during rotation of the shaft;
a first rotation mechanism which actuates rotation of the shaft; and
a control portion configured to store a program, accept data input, and display output, the control portion configured to control operation of the first rotation mechanism so as to rotate the filtering device to a first orientation in which the inflow port is vertically higher than the first outlet port for a first operation of the filtering device including filtering cells of a cell suspension and a second orientation in which the inflow port is vertically lower than the first outlet port for a second operation of the filtering device.

2. The concentrator according to claim 1 further comprising:
a culture vessel having a first port and a second port bringing an internal space and an outside into communication with each other;
a first reservoir having a third port bringing an internal space and the outside into communication with each other;
a collection vessel having a fourth port bringing an internal space and the outside into communication with each other; and
a liquid supply/discharge mechanism having a switching mechanism switching flow passages in the liquid supply circuit and the liquid discharge circuit, a first pump circulating a liquid in the liquid supply circuit, and a second pump circulating a fluid in the liquid discharge circuit, wherein
the liquid supply circuit is connected to the first port, the inflow port, and the third port so that the flow passages are switchable, and
the liquid discharge circuit is connected to the second port, the first outflow port, the second outflow port, and the fourth port so that the flow passages are switchable.

3. The concentrator according to claim 2 further comprising:
a second rotation mechanism that is coupled to the culture vessel and wherein the control portion is further configured to control operation of the second rotation mechanism so as to rotate the culture vessel so that positions in a vertical direction of the first port and the second port are changeable.

4. The concentrator according to claim 2, wherein the culture vessel is mechanically coupled to the shaft so that the shaft integrally rotates the culture vessel and the filtering device; and
wherein the control portion is further configured to control rotation of the culture vessel so that the positions in the vertical direction of the first port and the second port are changeable.

5. The concentrator according to claim 2, further comprising:
a second reservoir having a fifth port bringing an internal space and the outside into communication with each other and capable of reserving a priming liquid in the internal space; and
a third reservoir having a sixth port bringing an internal space and the outside into communication with each other and capable of reserving a culture medium in the internal space; and wherein
the control portion controls an operation of the liquid supply/discharge mechanism and the first rotation mechanism, wherein
the liquid supply circuit is connected to the fifth port and the sixth port so that flow passages are switchable, and
the control portion executes
a moving step of bringing the second port and the third port into communication with each other by the liquid supply/discharge mechanism, and then driving the first pump to thereby move the cell suspension to the first reservoir from the culture vessel,
a priming step of rotating the filtering device with the first rotation mechanism and shaft into a first state in which the inflow port is located downward relative to the first outflow port, bringing the fifth port and the inflow port into communication with each other by the liquid supply/discharge mechanism and opening the inflow port, and then driving at least the first pump to thereby supply the priming liquid to the filtering device from the second reservoir,
a filtering step of rotating the filtering device with the first rotation mechanism and shaft into a second state in which the inflow port is located upward relative to the first outflow port by the first rotation mechanism, bringing the third port and the inflow port into communication with each other by the liquid supply/discharge mechanism, closing the first outflow port and opening the second outflow port, and then driving at least the first pump to thereby supply the cell suspension to the filtering device from the first reservoir, and
a collecting step of bringing the sixth port and the inflow port into communication with each other by the liquid supply/discharge mechanism, closing the second outflow port and bringing the first outflow port and the fourth port into communication with each other, and then driving at least the first pump to thereby supply the cell suspension to the collection vessel from the filtering device.

6. The concentrator according to claim 5, wherein
the control portion rotates the culture vessel with the first rotation mechanism and shaft into a third state in which the first port is located downward relative to the second port in the moving step.

7. The concentrator according to claim 2, wherein
the culture vessel has a bag shape in which an internal space is formed with a flexible sheet.

8. The concentrator according to claim 7, wherein
an inner surface demarcating the internal space in the culture bag has cell adhesiveness suitable for culturing adhesive cells.

9. The concentrator according to claim 1, wherein the filtration membrane contains hollow fibers.

10. The concentrator according to claim 2 wherein the first pump and the second pump are tube pumps.

11. A method for concentrating a cell suspension using
a switching mechanism of switching flow passages in a liquid supply circuit connected to a first port bringing an internal space of a culture vessel and an outside into communication with each other, an inflow port bringing an inside of a filtration membrane of a filtering device having a case provided with the filtration membrane in an internal space and an outside of the case into communication with each other, a third port bringing an internal space of a first reservoir and the outside into communication with each other, a fifth port bringing an internal space of a second reservoir capable of reserving a priming liquid in the internal space and the outside into communication with each other, and a sixth port bringing an internal space of a third reservoir capable of reserving a culture medium in the internal space and the outside into communication with each other so that the flow passages are switchable, and to switch flow passages in a liquid discharge circuit connected to a second port bringing the internal space of the culture vessel and the outside into communication with each other, a first outflow port bringing the inside of the filtration membrane of the filtering device and the outside of the case into communication with each other, a second outflow port bringing the outside of the filtration membrane of the filtering device and the outside into communication with each other, and a fourth port bringing an internal space of a collection vessel and the outside into communication with each other so that the flow passages are switchable,
a liquid supply/discharge mechanism having a first pump circulating a liquid in the liquid supply circuit and a second pump circulating a liquid in the liquid discharge circuit,
a shaft that is rotatable and to which the filtering device is mechanically linked to rotate with the shaft so that positions in a vertical direction of the inflow port and the first outflow port change during rotation of the shaft,
a first rotation mechanism which actuates rotation of the shaft, and
a control portion configured to store a program, accept data input, and display output, the control portion configured to control operation of the switching mechanism, the liquid supply/discharge mechanism, and the first rotation mechanism, the control portion configured to implement the method comprising:
a moving step of bringing the second port and the third port into communication with each other, and then driving the first pump to thereby move a cell suspension to the first reservoir from the culture vessel;
a priming step of rotating the filtering device with the first rotation mechanism and shaft into a first state in which the inflow port is located downward relative to the first outflow port, bringing the fifth port and the inflow port into communication with each other and opening the inflow port, and then driving at least the first pump drive to thereby supply a priming liquid to the filtering device from the second reservoir;
a filtering step of rotating the filtering device with the first rotation mechanism and shaft into a second state in which the inflow port is located upward relative to the first outflow port, bringing the third port and the inflow port into communication with each other, closing the first outflow port and opening the second outflow port open, and then driving at least the first pump to thereby supply the cell suspension to the filtering device from the first reservoir; and
a collecting step of bringing the sixth port and the inflow port into communication with each other, closing the second outflow port and bringing the first outflow port and the fourth port into communication with each other, and then driving at least the first pump to thereby supply the cell suspension to the collection vessel from the filtering device.

12. The concentrator according to claim 3, further comprising:
a second reservoir having a fifth port bringing an internal space and the outside into communication with each other and capable of reserving a priming liquid in the internal space; and
a third reservoir having a sixth port bringing an internal space and the outside into communication with each other and capable of reserving a culture medium in the internal space; and wherein
the control portion controls an operation of the liquid supply/discharge mechanism and the first rotation mechanism, wherein
the liquid supply circuit is connected to the fifth port and the sixth port so that flow passages are switchable, and
the control portion executes
a moving step of bringing the second port and the third port into communication with each other by the liquid supply/discharge mechanism, and then driving the first pump to thereby move the cell suspension to the first reservoir from the culture vessel,
a priming step of rotating the filtering device with the first rotation mechanism and shaft into a first state in which the inflow port is located downward relative to the first outflow port, bringing the fifth port and the inflow port into communication with each other by the liquid supply/discharge mechanism and opening the inflow port, and then driving at least the first pump to thereby supply the priming liquid to the filtering device from the second reservoir,
a filtering step of rotating the filtering device with the first rotation mechanism and shaft into a second state in which the inflow port is located upward relative to the first outflow port by the first rotation mechanism, bringing the third port and the inflow port into communication with each other by the liquid supply/discharge mechanism, closing the first outflow port and opening the second outflow port, and then driving at least the first pump to thereby supply the cell suspension to the filtering device from the first reservoir, and
a collecting step of bringing the sixth port and the inflow port into communication with each other by the liquid supply/discharge mechanism, closing the second outflow port and bringing the first outflow port and the fourth port into communication with each other, and then driving at least the first pump to thereby supply the cell suspension to the collection vessel from the filtering device; and wherein the control portion rotates the culture vessel with the second rotation mechanism and shaft into a third state in which the first port is located downward relative to the second port in the moving step.

* * * * *